US006583156B1

(12) United States Patent
Gillespie et al.

(10) Patent No.: US 6,583,156 B1
(45) Date of Patent: Jun. 24, 2003

(54) 4-QUINOLINEMETHANOL DERIVATIVES AS PURINE RECEPTOR ANTAGONISTS (1)

(75) Inventors: Roger John Gillespie, Wokingham (GB); Joanne Lerpiniere, Wokingham (GB); Suneel Gaur, Wokingham (GB); David Reginald Adoms, Wokingham (GB); Lars Jacob Stray Knutsen, Wokingham (GB); Simon Edward Ward, Wokingham (GB)

(73) Assignee: Vernalis Research Limited, Wokingham (GB)

( * ) Notice: Subject to any disclaimer, the term of this patent is extended or adjusted under 35 U.S.C. 154(b) by 0 days.

(21) Appl. No.: 09/786,471

(22) PCT Filed: Sep. 3, 1999

(86) PCT No.: PCT/GB99/02923

§ 371 (c)(1),
(2), (4) Date: May 16, 2001

(87) PCT Pub. No.: WO00/13681

PCT Pub. Date: Mar. 16, 2000

(30) Foreign Application Priority Data

Sep. 4, 1998 (GB) ............................................. 96193824

(51) Int. Cl.$^7$ ...................... A61K 31/47; C07D 215/16; C07D 215/38
(52) U.S. Cl. ...................... 514/311; 514/312; 514/313; 514/314; 546/153; 546/159
(58) Field of Search ................ 546/153, 159; 514/312, 314, 313, 311

(56) References Cited

U.S. PATENT DOCUMENTS

| | | | |
|---|---|---|---|
| 4,070,469 A | | 1/1978 | Haber et al. ................ 424/258 |
| 5,047,534 A | | 9/1991 | Peet et al. ................... 544/267 |
| 5,733,572 A | * | 3/1998 | Unger |
| 6,117,884 A | | 9/2000 | Daeuble et al. ............. 514/311 |
| 6,191,105 B1 | * | 2/2001 | Ekwuribe |

FOREIGN PATENT DOCUMENTS

| | | |
|---|---|---|
| CH | 1 645 978 | 1/1971 |
| CH | 26 12 250 | 1/1977 |
| CH | 28 06 909 | 8/1978 |
| EP | 0 030 044 | 6/1981 |
| EP | 0 049 776 | 4/1982 |
| EP | 0 237 929 | 9/1987 |
| EP | 0 365 863 | 5/1990 |
| EP | 0 383 281 | 8/1990 |
| EP | 0 428 107 | 5/1991 |
| EP | 0 507 594 | 10/1992 |
| EP | 0 558 950 | 9/1993 |
| JP | 0 053 964 | 6/1982 |
| JP | 62-212370 | 9/1987 |
| JP | 4-95070 | 3/1992 |
| WO | 94/10164 | 5/1994 |
| WO | 96/02509 | 2/1996 |
| WO | 96/23777 | 8/1996 |
| WO | 97/23466 | 7/1997 |
| WO | 97/37999 | 10/1997 |
| WO | 9813047 | * 4/1998 |
| WO | 98/48784 | 11/1998 |
| WO | 98/54190 | 12/1998 |
| WO | 99/26627 | 6/1999 |

OTHER PUBLICATIONS

Liu et al., "Synthesis of 5,6–dihydro–4–hydroxy–2–prones via formal cycloaddition reactions", Tetrahedron Letter 41:3299–3302, (2000), Elsevier Science Ltd.

Maertens et al., "Inhibition of volume–regulated and calcium–activated chloride channels by the Antimalarial Mefloquine[1]", J. of Pharmacology and Experimental Therapeutics, 295:29–37, (2000), American Society for Pharmacology and Experimental Therapeutics.

Gribble et al., "The antimalarial agent mefloquine inhibits ATP–sensitive K–channels", British Journal of Pharm. 131:756–760, (2000), Macmillan Publishers Ltd.

Sit et al., "3–Hydroxy–Quinolin–2–ones: inhibitors of [$^3$H]–glycine binding to the site associated with the NMDA Receptor", Bioorganic & Medicinal Chemistry Letters, 6:499–504, (1996), Elsevier Science Ltd.

(List continued on next page.)

Primary Examiner—D. Margaret Seaman
(74) Attorney, Agent, or Firm—Foley & Lardner

(57) ABSTRACT

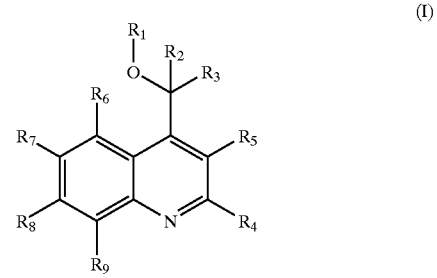

(I)

Use a compound of formula (I) wherein: $R_1$ is hydrogen or alkyl; $R_2$ and $R_3$ are independently selected from hydrogen, alkyl, aryl and heterocyclyle or together may form a ring or $R_1$ and $R_2$ or $R_3$ together may form an oxygen-containing, optionally fused ring pharmaceutically acceptable salts or prodrugs thereof, with the proviso that where $R_1$ and $R_4$ to $R_9$ are hydrogen, $R_2$ or $R_3$ is not 3-methoxy-4-benzyloxyphenyl or 2-dimethylaminoethoxymethyl, in the manufacture of a medicament for the treatment or prevention of a disorder in which the blocking of purine receptors, particularly adenosine receptors and more particularly $A_{2A}$ receptors, may be beneficial. Said disorders are neurodegenerative disorders or movement disorders selected from Parkinson's disease or progressive supernuclear palsy, Huntington's disease, multiple system atrophy, corticobasal degeneration, Wilson's disease, Hallerrorden-Spatz disease, progressive pallidal atrophy, Dopa-responsive dystonia-Parkinsonism, spasticity, Alzheimer's disease or other disorders of the basal ganglia which result in dyskinesias.

26 Claims, No Drawings

OTHER PUBLICATIONS

Lim et al, "The anticholnesterase activity of mefloquine", Clinical and Experimental Pharmacology & Physiology 12:527–531, (1985) Nat'l Univ. of Singapore.

Wesche et al., "Neurotoxicity of Artemisinin Analogs in Vitro", Antimicrobial Agents and Chemotherapy, 38:1813–1819, (1994), American Society for Microbiology.

McCaustland et al. "A structure modification study of the antimalarial 2-(p-Chlorophenyl)-2-(4-piperidyl) Tetrahydrofuran", J, of Medicinal Chemistry, 17:993–1000, Midwest research institute (1974).

Carroll et al, "4–substituted 5–[m–(Trifluoromehtyl)phenoxy]primaquine Analogues as potential antimalarial Agents", J. Med. Chem. 28:1564–1567, (1985), American Chemical Society.

Carroll et al., "Optical isomers of aryl–2–piperidylmethanol antimalarial agents.preparation, optical purity, and Absolute stereochemistry", J. Med. Chem., 17:210–219, (1974), American Chemical Society.

Patel et al. "Antimalarials. 6. Some new α–Alkylaminomethyl–4–quinolinemethanols", J. Med. Chem. 14:198–202, (1971), Dept. of Chemistry, Univ. of Virginia.

Patten et al., "Drug–induced depression", Psychotherapy and Psychosomatics, 66:63–73, (1997) S. Karger Ag.

Chien et al., "Difference in antimalarial activity between certain amino alcohol diastereomers", J. Med. Chem. 19:170–172, (1976), Midwest research Inst.

Blumbergs et al., "Antimalarials.7.2,8–Bits(trifluoromethyl)–4–quinolinemethanols", J. Med. Chem., 18:1122–1126, (1975), Starks Associates Inc.

Jauch et al., "Metabolismus von Ro 21–5998 (Mefloquin) bei der Ratte", Drug Research 30:60–67, (1980) XP–002110896.

Chen et al., "Structure–activity relationship of quinoline carboxyic acids", Biochem. Pharm., 40:709–714, (1990) Pergamon Press Inc.

Mestre et al., "1[4–(2–Ter–Butyl–Quinolyl)]–3–(4–Piperidyl) Propanol (PK 10139): A new potent and long–acting Antiarrhythic agent", J. Pharm. And Exper. Therapeutics, 225:158–163, (1983), Amer. Soc. For Pharm. & Experimental therapeutics.

Zymalkowski, "Die addition von Cyclohexanon an Chinolinaldehyde", Archiv der Pharmazie, 4:162–170, (1955) XP–000892336.

Franke et al., "Topological pharmacophores new methods and their application to a set of antimalarials", Struct. Act. Relat. 4:51–63, (1985), XP–0000900058.

Kim et al., "Quantitative structure–activity relationships in 1–aryl–2–(alkylamino)ethanol antimalarials", J. Med. Chem., 22:366–391, (1979), American Chemical Society.

Lynch et al., "Sodium channel blockers reduce oxygen–glucose deprivation–induced cortical neuronal injury When combined with glutamate receptor antagonists[1]", J. Pharm. Exp. Therap., 273:554–560, 1995.

Coleman, "Purine antagonists in the identification of adenosine–receptors in guinea–pig trachea and the role Of purines in non–adrenergic inhibitory neurotransmission", Br. J. Pharmac. 69:359–366, (1980), Macmillan J.

Akeson et al., "Suppression of interleukin–1β and LDL scavenger receptor expression in macrophages by a Selective protein C inhibitor", J. of Lipid Research, 32:1699–1707, (1991) Marion Merrell Dow Research Inst.

Wommack et al., "Potential antimalarials. IV.[1,2] Quinoline–α,α–dialkylmehtanols", J. Med. Chem., 13:383–386 (1969), Dept. of Chem. Vanderbilt Univ.

Schaefer et al., "Synthesis of Potential Antimalarials", (1970), pp. 607–613, XP–000915098.

Novotny et al., "Synthesis and screening of potential antimalarial agent α–(2–Piperidyl)–2–(1–adamantyl)–6, 8–Dichloro–4–quinolinemethanol Hydrochloride", J. of Pharm. Sciences, 63:1264–1267, (1994) Texas Research Inst.

Wetzel et al., "Antimalarials.9.α–(2–Piperidyl)–4–quinolinemethanols Carrying 2–Aroxy and 2–(p–Choloroanilino) Groups[†,1]", J. Med. Chem., 16:528–532, (1973), Dept of Chem. Univ of Virginia.

Pinder et al, "Antimalarials. II.[1a] α–(2–Piperidy)–and α–(2–Pyridyl)–2–trifluoromethyl–4–quinolinemethanols[1b]", Antimalarials II, pp. 267–269, (1967), XP–000877337.

Atkinson et al, "Antimalarials. II Quinolinemethanols with decreased phototoxicity", J. Med. Chem. 13:537–541 (1970), Arthur D. Little Onc.

Fugitt et al., "2–substituted cinchoninic acids as intermediates in Quinolinemethanol syntheses", J. Med. Chem. 16:875–879, (1973), Dept. of Chemistry, Univ. of Texas.

Epling et al. "Sulfur–containing 2–Arylquinolinenmethanols as potential antimalarials", J. Heterocyclic Chem.

Hsu et al., "Synthesis of 2–(4–Quinolyl) and 2–(3–quinolyl) chrome derivatives", J. Chinese Soc., 29:29–37 (1982), School of Pharmacy, Nat'l Univ of Taiwan.

Erzhanov et al, "Synthesis and cyclization of 1–methyl–4–3–(3–R–Phenylamino)propyn–1–yl)piperidin–4–ols" ZH. Org. Khim. vol. 25, No. 8, pp. 1729–1732, (1989) XP–000923476.

Erzhanov et al, "Synthesis of 4–substituted Quinolines", IZV. AKAD. NAUK KAZ. SSR, SER. KHIM., No. 1, pp. 85–87, (1990) XP–000923475.

* cited by examiner

4-QUINOLINEMETHANOL DERIVATIVES AS PURINE RECEPTOR ANTAGONISTS (1)

This application is a 371 of PCT/GB 99/02923, filed Sep. 3, 1999.

The present invention relates to 4-quinolinylmethanol derivatives and their use in therapy. In particular, the present invention relates to the treatment of disorders in which the reduction of purinergic neurotransmission could be beneficial. The invention relates in particular to adenosine receptors and particularly adenosine $A_{2A}$ receptors, and to the treatment of movement disorders such as Parkinson's disease.

Movement disorders constitute a serious health problem, especially amongst the elderly sector of the population. These movement disorders are often the result of brain lesions. Disorders involving the basal ganglia which result in movement disorders include Parkinson's disease, Alzheimer's disease, Huntington's chorea and Wilson's disease. Furthermore, dyskinesias often arise as sequelae of cerebral ischaemia and other neurological disorders.

There are four classic symptoms of Parkinson's disease: tremor, rigidity, akinesia and postural changes. The disease is also commonly associated with depression, dementia and overall cognitive decline. Parkinson's disease has a prevalence of 1 per 1,000 of the total population. The incidence increases to 1 per 100 for those aged over 60 years. Degeneration of dopaminergic neurones in the substantia nigra and the subsequent reductions in interstitial concentrations of dopamine in the striatum are critical to the development of Parkinson's disease. Some 80% of cells from the substantia nigra need to be destroyed before the clinical symptoms of Parkinson's disease are manifested.

Current strategies for the treatment of Parkinson's disease are based on transmitter replacement therapy (L-dihydroxyphenylacetic acid (L-DOPA)), inhibition of monoamine oxidase (e.g. Deprenyl®), dopamine receptor agonists (e.g. bromocriptine and apomorphine) and anticholinergics (e.g. benztrophine, orphenadrine). Transmitter replacement therapy in particular does not provide consistent clinical benefit, especially after prolonged treatment when "on-off" symptoms develop, and this treatment has also been associated with involuntary movements of athetosis and chorea, nausea and vomiting. Additionally current therapies do not treat the underlying neurodegenerative disorder resulting in a continuing cognitive decline in patients. Despite new drug approvals, there is still a medical need in terms of improved therapies for movement disorders, especially Parkinson's disease. In particular, effective treatments requiring less frequent dosing, effective treatments which are associated with less severe side-effects, and effective treatments which control or reverse the underlying neurodegenerative disorder, are required.

Blockade of $A_2$ adenosine receptors has recently been implicated in the treatment of movement disorders such as Parkinson's disease (Richardson, P. J. et al., *Trends Pharmacol. Sci.* 1997, 18, 338–344) and in the treatment of cerebral ischaemia (Gao, Y. and Phillis, J. W., *Life Sci.* 1994, 55, 61–65). The potential utility of adenosine $A_{2A}$ receptor antagonists in the treatment of movement disorders such as Parkinson's Disease has recently been reviewed (Mally, J. and Stone, T. W., *CNS Drugs*, 1998, 10, 311–320).

Adenosine is a naturally occurring purine nucleoside which has a wide variety of well-documented regulatory functions and physiological effects. The central nervous system (CNS) effects of this endogenous nucleoside have attracted particular attention in drug discovery, owing to the therapeutic potential of purinergic agents in CNS disorders (Jacobson, K. A. et al., *J. Med. Chem.* 1992, 35, 407–422). This therapeutic potential has resulted in considerable recent research endeavour within the field of adenosine receptor agonists and antagonists (Bhagwhat, S. S.; Williams, M. *Exp. Opin. Ther. Patents* 1995, 5, 547–558).

Adenosine receptors represent a subclass ($P_1$) of the group of purine nucleotide and nucleoside receptors known as purinoreceptors. The main pharmacologically distinct adenosine receptor subtypes are known as $A_1$, $A_{2A}$, $A_{2B}$ (of high and low affinity) and $A_3$ (Fredholn, B. B., et al., *Pharmacol. Rev.* 1994, 46, 143–156). The adenosine receptors are present in the CNS (Fredholm, B. B., *News Physiol. Sci.*, 1995, 10, 122–128).

The design of $P_1$ receptor-mediated agents has been reviewed (Jacobson, K. A., Suzuki, F., *Drug Dev. Res.*, 1997, 39, 289–300; Baraldi, P. G. et al., *Curr. Med. Chem.* 1995, 2, 707–722), and such compounds are claimed to be useful in the treatment of cerebral ischemia or neurodegenerative disorders, such as Parkinson's disease (Williams, M. and Bumnstock, G. *Purinergic Approaches Exp. Ther.* (1997), 3–26. Editor: Jacobson, Kenneth A.; Jarvis, Michael F. Publisher: Wiley-Liss, New York, N.Y.)

The pharmacology of adenosine $A_{2A}$ receptors has been reviewed (Ongini, E.; Fredholm, B. B. *Trends Pharmacol. Sci.* 1996, 17(10), 364–372). One potential underlying mechanism in the aforementioned treatment of movement disorders by the blockade of $A_2$ adenosine receptors is the evidence of a functional link between adenosine $A_{2A}$ receptors to dopamine $D_2$ receptors in the CNS. Some of the early studies (e.g. Ferre, S. et al., Stimulation of high-affinity adenosine $A_2$ receptors decreases the affinity of dopamine $D_2$ receptors in rat striatal membranes. *Proc. Natl. Acad. Sci. U.S.A.* 1991, 88, 7238–41) have been summarised in two more recent articles (Fuxe, K. et al., *Adenosine Adenine Nucleotides Mol. Biol. Integr. Physiol.*, [Proc. Int. Symp.], 5th (1995), 499–507. Editors: Belardinelli, Luiz; Pelleg, Amir. Publisher: Kluwer, Boston, Mass.; Ferre, S. et al., *Trends Neurosci.* 1997, 20, 482–487).

As a result of these investigations into the functional role of adenosine $A_{2A}$ receptors in the CNS, especially in vivo studies linking $A_2$ receptors with catalepsy (Ferre et al., *Neurosci. Lett.* 1991, 130, 1624; Mandhane, S. N. et al., *Eur. J. Pharmacol.* 1997, 328, 135–141) investigations have been made into agents which selectively bind to adenosine $A_{2A}$ receptors as potentially effective treatments for Parkinson's disease.

While many of the potential drugs for treatment of Parkinson's disease have shown benefit in the treatment of movement disorders, an advantage of adenosine $A_{2A}$ antagonist therapy is that the underlying neurodegenerative disorder is also treated. The neuroprotective effect of adenosine $A_{2A}$ antagonists has been reviewed (Ongini, E.; Adami, M.; Ferri, C.; Bertorelli, R., *Ann. N. Y. Acad. Sci.* 1997, 825 (Neuroprotective Agents), 30–48).

Xanthine derivatives have been disclosed as adenosine $A_2$ receptor antagonists as useful for treating various diseases caused by hyperfunctioning of adenosine $A_2$ receptors, such as Parkinson's disease (see, for example, EP-A-565377).

One prominent xanthine-derived adenosine $A_{2A}$ selective antagonist is CSC [8-(3-chlorostyryl)caffeine] (Jacobson et al., *FEBS Lett.*, 1993, 323, 141–144).

Theophylline (1,3-dimethylxanthine), a bronchodilator drug which is a mixed antagonist at adenosine $A_1$ and $A_{2A}$ receptors, has been studied clinically. To determine whether a formulation of this adenosine receptor antagonist would be of value in Parkinson's disease an open trial was conducted on 15 Parkinsonian patients, treated for up to 12 weeks with a slow release oral theophylline preparation (150 mg/day), yielding serum theophylline levels of 4.44 mg/L after one week. The patients exhibited significant improvements in mean objective disability scores and 11 reported moderate or marked subjective improvement (Mally, J., Stone, T. W. *J. Pharm. Pharmacol.* 1994,46, 515–517).

KF 17837 [(E)-8-(3,4-dimethoxystyryl)-1,3-dipropyl-7-methylxanthine] is a selective adenosine $A_{2A}$ receptor antagonist which on oral administration significantly ameliorated the cataleptic responses induced by intracerebroventricular administration of an adenosine $A_{2A}$ receptor agonist, CGS 21680. KF 17837 also reduced the catalepsy induced by haloperidol and reserpine. Moreover, KF 17837 potentiated the anticataleptic effects of a subthreshold dose of L-DOPA plus benserazide, suggesting that KF 17837 is a centrally active adenosine $A_{2A}$ receptor antagonist and that the dopaminergic function of the nigrostriatal pathway is potentiated by adenosine $A_{2A}$ receptor antagonists (Kanda, T. et al., *Eur. J. Pharmacol.* 1994, 256, 263–268). The structure activity relationship (SAR) of KF 17837 has been published (Shimada, J. et al., *Bioorg. Med. Chem. Lett.* 1997, 7, 2349–2352). Recent data has also been provided on the $A_{2A}$ receptor antagonist KW-6002 (Kuwana, Y et al., *Soc. Neurosci. Abstr.* 1997, 23, 119.14; and Kanda, T. et al., *Ann. Neurol.* 1998, 43(4), 507–513).

New non-xanthine structures sharing these pharmacological properties include SCH 58261 and its derivatives (Baraldi, P. G. et al., Pyrazolo[4,3-e]-1,2,4-triazolo[1,5-c] pyrimidine Derivatives: Potent and Selective $A_{2A}$ Adenosine Antagonists. *J. Med. Chem.* 1996, 39, 1164–71). SCH 58261 (7-(2-phenylethyl)-5-amino-2-(2-furyl)-pyrazolo-[4,3-e]-1, 2,4-triazolo[1,5-c] pyrimidine) is reported as effective in the treatment of movement disorders (Ongini, *E. Drug Dev. Res.* 1997, 42(2), 63–70) and has been followed up by a later series of compounds (Baraldi, P. G. et al., *J. Med. Chem.* 1998, 41(12), 2126–2133).

The foregoing discussion indicates that a potentially effective treatment for movement disorders in humans would comprise agents which act as antagonists at adenosine $A_{2A}$ receptors.

It has now been found that 4-quinolinemethanol derivatives, which are structurally unrelated to known adenosine receptor antagonists, exhibit unexpected antagonist binding affinity at adenosine ($P_1$) receptors, and in particular at the adenosine $A_{2A}$ receptor. Such compounds may therefore be suitable for the treatment of movement disorders, such as disorders of the basal ganglia which result in dyskinesias. These may include Parkinson's disease, Alzheimer's disease, spasticity, Huntingdon's chorea and Wilson's disease.

According to the present invention there is provided use of a compound of formula (I):

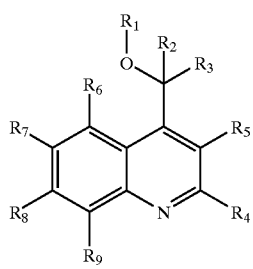

I wherein:
$R_1$ is hydrogen or alkyl;
$R_2$ and $R_3$ are independently selected from hydrogen, alkyl, aryl and 4, 5, 6, 7 or 8 membered unbridged saturated and partially unsaturated heterocyclic rings containing one or more heteroatoms selected from O, S and N, or together may form a 3, 4, 5, 6 or 7 membered saturated or partially unsaturated carbocyclic ring or a 3, 4, 5, 6, 7 or 8 membered saturated or partially unsaturated heterocyclic ring containing one or more heteroatoms selected from O, S and N;

or $R_1$ and $R_2$ or $R_3$ together may form a 3, 4, 5, 6, 7 or 8 membered oxygen-containing saturated or partially unsaturated heterocyclic ring optionally containing one or more additional heteroatoms selected from O, S and N;

or $R_1$ and $R_2$ and $R_3$ together may form a 4, 5, 6, 7 or 8 membered oxygen-containing partially unsaturated or aromatic heterocyclic ring optionally containing one or more additional heteroatoms selected from O, S and N in which $R_2$ and $R_3$ together form a double bond;

wherein said carbocyclic ring or said heterocyclic ring when partially unsaturated may be fused to an aryl ring; and $R_4, R_5, R_6, R_7, R_8$ and $R_9$ are independently selected from hydrogen, alkyl, aryl, 4, 5, 6, 7 or 8 membered saturated and partially unsaturated heterocyclic rings containing one or more heteroatoms selected from O, S and N, hydroxy, halogen, nitro, cyano, alkoxy, aryloxy, $COR_{10}$, $OCOR_{10}$, $CO_2R_{10}$, $SR_{10}$, $SOR_{10}$, $SO_2R_{10}$, $SO_2NR_{10}R_{11}$, $CONR_{10}R_{11}$, $CONR_{10}NR_{11}R_{12}$, $OCONR_{10}R_{11}$, $NR_{10}R_{11}$, $NR_{10}COR_{11}$, $NR_{10}CONR_{11}R_{12}$, $NR_{10}CO_2R_{11}$, $NR_{10}SO_2R_{11}$, $CR_{10}NOR_{11}$, $NR_{10}CONR_{11}NR_{12}R_{13}$, $NR_{10}NR_{11}CO_2R_{12}$, $NR_{10}NR_{11}CONR_{12}R_{13}$, $NR_{10}NR_{11}COR_{12}$, $NR_{10}NR_{11}SO_2R_{12}$, $SO_2NR_{10}NR_{11}R_{12}$, $NR_{10}SO_2NR_{11}NR_{12}R_{13}$ and $NR_{10}SO_2NR_{11}R_{12}$ wherein $R_{10}, R_{11}, R_{12}$ and $R_{13}$ are independently selected from hydrogen, alkyl and aryl, or a pharmaceutically acceptable salt or prodrug thereof, with the proviso that where $R_1$ and $R_4$ to $R_9$ are hydrogen, $R_2$ or $R_3$ is not 3-methoxy-4-benzyloxyphenyl or 2-dimethylaminoethoxymethyl, in the manufacture of a medicament for the treatment or prevention of a disorder in which the blocking of purine receptors, particularly adenosine receptors and more particularly $A_{2A}$ receptors, may be beneficial.

As used herein, the term "alkyl" means a branched or unbranched, cyclic or acyclic, saturated or unsaturated (e.g. alkenyl or alkynyl) hydrocarbyl radical. Where cyclic, the alkyl group is preferably $C_3$ to $C_{12}$, more preferably $C_5$ to $C_{10}$, more preferably $C_5$, $C_6$ or $C_7$. Where acyclic, the alkyl group is preferably $C_1$ to $C_{10}$, more preferably $C_1$ to $C_6$, more preferably methyl, ethyl, n-propyl, isopropyl, n-butyl, isobutyl or t-butyl.

As used herein, the term "aryl" means an aromatic group, such as phenyl or naphthyl, or a heteroaromatic group containing one or more heteroatom, such as pyridyl, pyrrolyl, quinolinyl, furanyl, thienyl, oxadiazolyl, thiadiazolyl, thiazolyl, oxazolyl, isoxazolyl, pryazolyl, triazolyl, imidazolyl or pyrimidinyl.

The alkyl and aryl groups may be substituted or unsubstituted. Where any of $R_2$ to $R_9$ are selected from 4, 5, 6, 7 or 8 membered saturated or partially-unsaturated heterocyclic rings, the ring may be substituted or unsubstituted. Where $R_2$ and $R_3$ together form a carbocyclic or heterocyclic ring, the ring may be substituted or unsubstituted. Where $R_1$ and $R_2$ and/or $R_3$ together form an oxygen-containing heterocyclic ring, the ring may be substituted or unsubstituted. Where substituted, there will generally be 1 to 3 substituents present, preferably 1 substituent. Substituents may include: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxy, hydroxyalkyl, aryl(hydroxy)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylamninocarbonyloxy, arylaminocarbonyloxy)

and ureas (e.g. mono- or di-alkylaminocarbonylamino or arylaminocarbonylamino);

nitrogen-containing groups such as amines (e.g. amino, mono- or di-alkylamino, aminoalkyl, mono- or di-alkylaminoalkyl), azides, nitriles (e.g. cyano, cyanoalkyl), nitro;

sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl);

and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuiranyl, isobenzofimranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

As used herein, the term "alkoxy" means alkyl-O— and "alkoyl" means alkyl-CO—. Alkoxy substituent groups or alkoxy-containing substituent groups may be substituted by one or more alkyl groups.

As used herein, the term "halogen" means a fluorine, chlorine, bromine or iodine radical, preferably a fluorine, chlorine or bromine radical.

As used herein the term "prodrug" means any pharmaceutically acceptable prodrug of the compound of formula (I).

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are hydrochloric, hydrobromic, phosphoric, sulfuric and methanesulfonic acids, and most particularly preferred is the hydrochloric salt. Acceptable base salts include alkali metal (e.g. sodium, potassium), alkaline earth metal (e.g. calcium, magnesium) and aluminium salts.

As used herein, the term "saturated heterocyclic ring" means a heterocyclic ring wherein the bonds between the atoms forming the ring are single bonds. Examples of such saturated heterocyclic rings include aziridinyl, azetidinyl, pyrrolidinyl, piperidinyl, hexahydroazepinyl, heptamethyleneiminyl, oxiranyl, oxetanyl tetrahydrofuranyl, tetrahydropyranyl, tetrahydrothiophenyl, tetrahydrothiopyran, piperazinyl, morpholinyl, dioxanyl and thiomorpholinyl As used herein, the term "partially unsaturated heterocyclic ring" means a heterocyclic ring wherein one or more of the bonds between the atoms forming the ring are unsaturated bonds and wherein the ring is non-aromatic in character. Examples of such partially unsaturated rings include 3-pyrrolinyl, imidazolinyl, oxazolinyl, thiazolinyl, pyrrazolinyl, dihydropyranyl, pyranyl, dihydropyridinyl and tetrahydropyridinyl.

As used herein, the term "carbocyclic ring" means a ring wherein the atoms forming the ring are carbon atoms and wherein the ring is either (a) a saturated ring in which the bonds between the ring atoms are single bonds (such as cyclopropyl, cyclobutyl, cyclopentyl, cyclohexyl, cycloheptyl and cyclooctyl; or a bicyclic ring such as norbornanyl); or (b) a partially unsaturated ring wherein one or more of the bonds between the ring atoms are unsaturated bonds and wherein the ring is non-aromatic in character (such as cyclopentenyl, cyclohexenyl, cycloheptenyl, cyclooctenyl, cyclopentadienyl, cyclohexadienyl and cycloheptadienyl); or (c) an aromatic ring (such as phenyl).

As used herein, the term "unbridged" refers to a ring or ring system which is not bridged; the term "bridged" referring to a ring system in which two or more rings share non-adjacent atoms to form a multicyclic ring system. Examples of a bridged ring system include adamantane, norbornane and 5-ethenyl-1-azabicyclo[2.2.2]octane.

As used herein, the term "fused" refers to a ring system in which two rings or ring systems share only adjacent ring atoms. Examples of a fused ring system include naphthalene, quinoline, indan and benzofuran.

Where any of $R_2$ to $R_9$ are selected from 4, 5, 6, 7 or 8 membered heterocyclic rings containing a plurality of heteroatoms selected from O, S and N, the heteroatoms may be the same or different.

Where $R_2$ and $R_3$ together form a 3, 4, 5, 6, 7 or 8 membered heterocyclic ring containing a plurality of heteroatoms selected from O, S and N, the heteroatoms may be the same or different.

Where $R_1$ and $R_2$ and/or $R_3$ form an oxygen-containing ring containing one or more additional heteroatoms selected from O, S and N, the heteroatoms in said ring may be the same or different.

Where $R_1$ and $R_2$; or $R_1$ and $R_3$; or $R_2$ and $R_3$ together form a 3 membered heterocyclic ring, it is preferred that said ring is saturated and contains no more than one heteroatom.

In an embodiment of the invention, $R_1$ is hydrogen or alkyl and $R_2$ and $R_3$ are independently selected from hydrogen, alkyl (including cycloalkyl, ara-alkyl and heteroara-alkyl), aryl (including heteroaryl) and 4, 5, 6, 7 or 8 membered unbridged saturated and partially unsaturated heterocyclic rings containing one or more heteroatoms selected from O, S and N, wherein said heterocyclic ring when partially unsaturated may be fused to an aryl ring.

In an alternative embodiment of the invention, $R_1$ is hydrogen or alkyl and $R_2$ and $R_3$ together form a 3, 4, 5, 6 or 7 membered saturated or partially unsaturated carbocyclic ring or a 3, 4, 5, 6, 7 or 8 membered saturated or partially unsaturated heterocyclic ring containing one or more heteroatoms selected from O, S and N, wherein said carbocyclic or heterocyclic ring when partially unsaturated may be fused to an aryl ring.

In a further alternative embodiment of the invention, $R_1$ and either $R_2$ or $R_3$ together form a 3, 4, 5, 6, 7 or 8-membered oxygen-containing saturated or partially unsaturated heterocyclic ring optionally containing one or more additional heteroatoms selected from O, S and N, wherein said heterocyclic ring when partially unsaturated may be fused to an aryl ring. In this embodiment, the $R_2$ or $R_3$ group which has not formed said heterocyclic ring with $R_1$ is selected from hydrogen, alkyl, aryl and 4, 5, 6, 7 or 8-membered unbridged saturated or partially unsaturated heterocyclic rings containing one or more heteroatoms selected from O, S and N, wherein said heterocyclic ring when partially unsaturated may be fused to an aryl ring.

In a further alternative embodiment of the invention, $R_1$ and $R_2$ and $R_3$ together form a 4, 5, 6, 7 or 8 membered oxygen-containing partially unsaturated or aromatic heterocyclic ring optionally containing one or more additional heteroatoms selected from O, S and N in which $R_2$ and $R_3$ together form a double bond, wherein said heterocyclic ring may be fused to an aryl ring. In this embodiment, preferably said oxygen-containing heterocyclic ring is aromatic.

In the compounds of formula (I), where $R_2$ and $R_3$ are independently selected from unbridged saturated and partially unsaturated heterocyclic rings, said heterocyclic ring is preferably a heterocyclic ring in which the one or more heteroatoms are selected only from O and S; is preferably monocyclic; and is preferably a 5 or 6-membered ring. Where said heterocyclic ring is partially unsaturated and is fused to an aryl ring, said aryl ring is preferably a phenyl ring.

In the compounds of formula (I), where $R_2$ and $R_3$ together form a carbocyclic ring, said carbocyclic ring is preferably unbridged; preferably monocyclic; and is preferably a 5 or 6-membered ring. Where said carbocyclic ring is partially unsaturated and is fused to an aryl ring, said aryl ring is preferably a phenyl ring.

In the compounds of formula (I), where $R_2$ and $R_3$ together form a heterocyclic ring, said heterocyclic ring is preferably a heterocyclic ring in which the one or more heteroatoms are selected only from O and S; is preferably unbridged; is preferably monocyclic; and is preferably a 4, 5 or 6-membered ring. Where said heterocyclic ring is partially unsaturated and is fused to an aryl ring, said aryl ring is preferably a phenyl ring.

In the compounds of formula (I) where $R_1$ and $R_2$ or $R_3$ together form a heterocyclic ring, said heterocyclic ring is preferably a heterocyclic ring in which the one or more heteroatoms are selected only from O and S; is preferably unbridged; and is preferably monocyclic. It is preferred that this heterocyclic ring contains 3, 4, 5 or 6 ring atoms, preferably 3, 5 or 6 ring atoms. Where the heterocyclic ring is partially unsaturated and is fused to an aryl ring, said aryl ring is preferably a phenyl ring.

In the compounds of formula (a) where $R_1$ and $R_2$ and $R_3$ together form a heterocyclic ring, said heterocyclic ring is preferably a heterocyclic ring in which the one or more heteroatoms are selected only from O and S; is preferably unbridged; and is preferably monocyclic. It is preferred that this heterocyclic ring contains 4, 5 or 6 ring atoms, preferably 5 or 6 ring atoms. Where the heterocyclic ring is fused to an aryl ring, said aryl ring is preferably a phenyl ring.

Preferably, the compounds of formula (I) are selected from compounds in which $R_1$ is hydrogen or methyl.

Preferably, the compounds of formula (I) are selected from compounds in which $R_2$ is hydrogen or methyl or compounds in which $R_2$ together with $R_3$ forms a ring, as defined above.

In the compounds of formula (I), where $R_2$ and/or $R_3$ is selected from alkyl, then preferably $R_2$ and/or $R_3$ is selected from methyl, isopropyl, cyclohexyl and benzyl. In one embodiment, at least one of $R_2$ and $R_3$ is selected from alkyl, aryl and heterocyclic rings as defined above, and preferably from alkyl.

In the compounds of formula (I), where $R_2$ and/or $R_3$ is selected from aryl, then preferably $R_2$ and/or $R_3$ is selected from 5 or 6-membered aromatic rings. In an embodiment of the invention, $R_2$ and/or $R_3$ is selected from carbocyclic aromatic rings and heteroaromatic rings containing heteroatoms other than nitrogen. In a further embodiment, $R_2$ and/or $R_3$ is selected from phenyl, 2-thienyl, 3-thienyl, 2-furyl, 3-furyl and 2-pyridyl, more preferably from phenyl, 2-thienyl, 3-thienyl, 2-furyl and 3-furyl, and more preferably from 2-thienyl, 3-thienyl, 2-furyl and 3-furyl.

In the compounds of formula (I), it is preferred that where one or both of $R_2$ and $R_3$ is selected from aryl, then said aryl is other than 3-methoxy-4-benzyloxyphenyl, preferably other than alkoxy-substituted phenyl, preferably other than alkoxy-substituted aryl. Where one or both of $R_2$ and $R_3$ is selected from alkyl, it is preferred that said alkyl group is other than 2-dimethylaminoethoxymethyl, preferably other than an ethoxymethyl group, preferably other than an alkoxymethyl group, and preferably other than an alkoxyalkyl group, particularly wherein said ethoxymethyl or said alkoxymethyl or said alkoxyalkyl group is substituted and more particularly wherein said ethoxymethyl or said alkoxymethyl or said alkoxyalkyl is substituted by a nitrogen-containing group (such as amino, amino or a nitrogen-containing heterocyclic group).

$R_4$, $R_5$, $R_6$, $R_7$, $R_8$ and $R_9$ are independently selected from hydrogen, alkyl (including cycloalkyl, halo-alkyl (such as trifluoromethyl), ara-alkyl and heteroara-alkyl), aryl (including heteroaryl), 4, 5, 6, 7 or 8 membered saturated and partially unsaturated heterocyclic rings containing one or more heteroatoms selected from O, S and N, hydroxy, halogen, nitro, cyano, alkoxy (including fluorinated alkoxy), aryloxy, $COR_{10}$, $OCOR_{10}$, $CO_2R_{10}$, $SR_{10}$, $SOR_{10}$, $SO_2R_{10}$, $SO_2NR_{10}R_{11}$, $CONR_{10}R_{11}$, $CONR_{10}NR_{11}R_{12}$, $OCONR_{10}OR_{11}$, $NR_{10}R_{11}$, $NR_{10}COR_{11}$, $NR_{10}CONR_{11}R_{12}$, $NR_{10}CO_2R_{11}$, $NR_{10}SO_2R_{11}$, $CR_{10}NOR_{11}$, $NR_{10}CONR_{11}NR_{12}R_{13}$, $NR_{10}NR_{11}CO_2R_{12}$, $NR_{10}NR_{11}CONR_{12}R_{13}$, $NR_{10}NR_{11}COR_{12}$, $NR_{10}NR_{11}SO_2R_{12}$, $SO_2NR_{10}NR_{11}R_{12}$, $NR_{10}SO_2NR_{11}NR_{12}R_{13}$ and $NR_{10}SO_2NR_{11}R_{12}$ wherein $R_{10}$, $R_{11}$, $R_{12}$ and $R_{13}$ are independently selected from hydrogen, alkyl and aryl.

In one embodiment of the invention, $R_4$, $R_5$, $R_6$, $R_7$, $R_8$ and $R_9$ are independently selected from hydrogen; alkyl (including cycloalkyl, halo-alkyl (such as trifluoromethyl), ara-alkyl and heteroara-alkyl); aryl (including heteroaryl); 4, 5, 6, 7 or 8 membered saturated heterocyclic rings containing one or more heteroatoms selected from O, S and N; hydroxy; halogen; nitro; cyano; alkoxy (including fluorinated alkoxy); aryloxy; $COR_{10}$; $OCOR_{10}$; $CO_2R_{10}$; $SR_{10}$; $SOR_{10}$; $SO_2R_{10}$; $SO_2NR_{10}R_{11}$; $CONR_{10}R_{11}$; $CONR_{10}NR_{11}R_{12}$; $OCONR_{10}R_{11}$; $NR_{10}COR_{11}$; $NR_{10}CONR_{11}$; $NR_{10}CONR_{11}R_{12}$; $NR_{10}CO_2R_{11}$; $NR_{10}SO_2R_{11}$; $CR_{10}NOR_{11}$; $NR_{10}CONR_{11}NR_{12}R_{13}$; $NR_{10}NR_{11}CO_2R_{12}$; $NR_{10}NR_{11}CONR_{12}R_{13}$; $SO_2NR_{10}NR_{11}R_{12}$; $NR_{10}SO_2NR_{11}NR_{12}R_{13}$; and $NR_{10}SO_2NR_{11}R_{12}$, wherein $R_{10}$, $R_{11}$, $R_{12}$ and $R_{13}$ are independently selected from hydrogen, alkyl and aryl.

In an embodiment of the invention, where any of $R_4$ to $R_9$ are selected from heterocyclic rings, said ring is unbridged and preferably monocyclic. In a further embodiment of the invention, where any of $R_4$ to $R_9$ are independently selected from $NR_{10}COR_{11}$ then $R_{10}$ of the or each $NR_{10}COR_{11}$, group is hydrogen.

It is preferred that at least one of $R_4$ to $R_9$ is a group other than hydrogen.

In an embodiment of the invention, the compounds of formula (I) are selected from compounds other than compounds in which both $R_4$ and $R_9$ are halo-alkyl (including trifluoromethyl). In an embodiment of the invention, $R_4$ and/or $R_9$ are independently selected from hydrogen, alkyl (preferably unsubstituted alkyl and preferably methyl or ethyl), aryl (preferably phenyl), alkoxy (preferably methoxy), hydroxy, halogen, $NR_{10}R_{11}$ (preferably where $R_{10}$ and $R_{11}$ are independently selected from hydrogen and alkyl (including cycloalkyl and ara-alkyl), preferably methyl, cyclohexyl or benzyl), $COR_{10}$ (preferably where $R_{10}$ is selected from hydrogen and alkyl (preferably methyl)), $CO_2R_{10}$ (preferably where $R_{10}$ is hydrogen or alkyl, preferably methyl), $SR_{10}$ (Preferably where $R_{10}$ is alkyl, preferably methyl), $SO_2R_{10}$ (preferably where $R_{10}$ is alkyl, preferably methyl) and $CONR_{10}R_{11}$ (preferably where $R_{10}$ and $R_{11}$ are independently selected from hydrogen and alkyl (including ara-alkyl), preferably methyl).

Preferably, the compounds of formula (I) are selected from compounds in which $R_5$ is hydrogen or alkyl, preferably hydrogen or methyl. Preferably, the compounds of formula (I) are selected from compounds in which $R_6$, $R_7$ and/or $R_9$ is hydrogen.

In an embodiment of the invention, the compounds of formula (I) are selected from:

2,8-bis(trifluoromethyl)-α-(3-thienyl)-4-quinolinemethanol;
2,8-bis(trifluoromethyl)-α-cyclohexyl-4-quinolinemethanol;
2,8-bis(trifluoromethyl)-α-(2,6-dichlorophenyl)-4-quinolinemethanol;
2,8-bis(trifluoromethyl)-α-(2-bromophenyl)-4-quinolinemethanol;
2,8-bis(trifluoromethyl)-α-(2-methoxyphenyl)-4-quinolinemethanol;
8-methyl-α-(3-thienyl)-2-trifluoromethyl-4-quinolinemethanol;
α-cyclohexyl-8-methyl-2-trifluoromethyl-4-quinolinemethanol, and
α-cyclohexyl-2-hydroxy-4-quinolinemethanol.

Where chiral, the compounds of formula (I) may be in the form of a racemic mixture of pairs of enantiomers or in enantiomerically pure form.

According to a further aspect of the present invention there is provided a method of treating or preventing a disorder in which the blocking of purine receptors, particularly adenosine receptors and more particularly adenosine $A_{2A}$ receptors, may be beneficial, the method comprising administration to a subject in need of such treatment an effective dose of a compound of formula (I) or a pharmaceutically acceptable salt or prodrug thereof.

The disorder may be caused by the hyperfunctioning of the purine receptors.

According to a further aspect of the present invention there is provided use of a compound of formula (I) or a pharmaceutically acceptable salt or prodrug thereof in the manufacture of a medicament for the treatment or prevention of movement disorders in a subject.

According to a further aspect of the invention there is provided a method of treating or preventing movement disorders comprising administration to a subject in need of such treatment an effective dose of a compound of formula (I) or a pharmaceutically acceptable salt or prodrug thereof.

According to a further aspect of the invention there is provided use of a compound of formula (I) or a pharmaceutically acceptable salt or prodrug thereof in the manufacture of a medicament for neuroprotection in a subject.

According to a further aspect of the invention there is provided a method of neuroprotection comprising administration to a subject in need of such treatment an effective dose of a compound of formula (I) or a pharmaceutically acceptable salt or prodrug thereof.

The medicament for or method of neuroprotection may be of use in the treatment of subjects who are suffering from or at risk from a neurodegenerative disorder, such as a movement disorder.

According to a further aspect of the invention, there is provided for use in therapy a compound of formula (I), or a pharmaceutically acceptable salt or prodrug thereof, other than:

(i) compounds in which $R_2$ and $R_3$ are selected from methyl, phenyl and substituted phenyl, $R_4$ is phenyl or substituted phenyl and $R_1$ and $R_5$ to $R_9$ are hydrogen;

(ii) compounds in which $R_2$ or $R_3$ is methyl or isopropyl and $R_4$ and $R_9$ are $CF_3$;

(iii) compounds in which $R_2$ or $R_3$ is acyclic $C_1$ to $C_5$ alkyl substituted by phenyl or by an N-containing heterocycle or by a mono- or di-alkyl amino group or by a (dialkylamino)alkoxy group;

(iv) compounds in which $R_2$ or $R_3$ is pyridyl, indole, pyrimidine, piperidine, piperazine or pyrrolidine;

(v) compounds in which $R_4$ is thienyl and $R_1$ to $R_3$ and $R_5$ to $R_9$ are hydrogen;

(vi) compounds in which $R_1$ and either $R_2$ or $R_3$ together form a 3-membered oxygen-containing saturated heterocyclic ring; and (vii) compounds in which $R_1$ and $R_2$ and $R_3$ together form a 5-membered oxygen-containing partially-unsaturated or aromatic heterocyclic ring.

In an alternative embodiment, there is provided for use in therapy a compound of formula (I), or a pharmaceutically acceptable salt or prodrug thereof, other than:

(i) compounds in which $R_2$ and $R_3$ are selected from methyl, phenyl and substituted phenyl;

(ii) compounds in which $R_2$ or $R_3$ is acyclic saturated alkyl and $R_4$ and $R_9$ are $CF_3$;

iii) compounds in which $R_2$ or $R_3$ is alkyl substituted by phenyl or by an N-containing heterocycle or by a mono- or di-alkyl amino group or by a (dialkylamino) alkoxy group;

iv) compounds in which $R_2$ or $R_3$ is a heterocyclic ring in which the ring atoms are selected only from carbon and nitrogen;

v) compounds in which $R_4$ is thienyl;

vi) compounds in which $R_1$ and either $R_2$ or $R_3$ together form an oxygen-containing saturated heterocyclic ring; and vii) compounds in which $R_1$ and $R_2$ and $R_3$ together form an oxygen-containing partially unsaturated or aromatic heterocyclic ring.

In a further alternative embodiment, there is provided for use in therapy a compound of formula (I), or a pharmaceutically acceptable salt or prodrug thereof, other than:

(i) compounds in which $R_2$ and $R_3$ are selected from carbocyclic aromatic groups;

(ii) compounds in which $R_2$ and/or $R_3$ are selected from acyclic saturated alkyl;

(iii) compounds in which $R_2$ or $R_3$ is alkyl substituted by aryl or by a saturated N-containing heterocycle or by a mono- or di-alkyl amino group or by a (dialkylamino)alkoxy group;

(iv) compounds in which $R_2$ or $R_3$ is an N-containing heterocyclic ring;

(v) compounds in which $R_4$ is an S-containing heterocyclic ring; and (vi) compounds in which $R_1$ and $R_2$ and/or $R_3$ together form an oxygen-containing heterocyclic ring.

According to a further aspect of the invention, there is provided for use in therapy a compound of formula (I), or a pharmaceutically acceptable salt or prodrug thereof, wherein:

(i) $R_3$ is a 5 or 6 membered unbridged saturated, partially-unsaturated or aromatic heterocyclic ring in which the one or more heteroatoms are selected only from O and S; or (ii) $R_3$ is a 3, 4, 5, 6 or 7 membered carbocyclic ring; or (iii) $R_2$ and $R_3$ together form a 3, 4, 5 or 7 membered saturated or partially-unsaturated carbocyclic ring, or a 4, 5, 6 or 7 membered saturated or partially-unsaturated heterocyclic ring in which the one or more heteroatoms are selected only from O and S, or a 4, 5 or 7 membered saturated or partially unsaturated heterocyclic ring containing one or more heteroatoms selected from N, and preferably a 3, 4, 5 or 7 membered saturated or partially-unsaturated carbocyclic ring or a 4, 5, 6 or 7 membered saturated or partially unsaturated heterocyclic ring in which the one or more heteroatoms are selected only from O and S; or (iv) $R_1$ is $C_1$ to $C_4$ acyclic alkyl and $R_3$ is aryl (including heteroaryl) or $C_3$ to $C_7$ cycloalkyl; or (v) $R_1$ is $C_1$ to $C_4$ acyclic alkyl and $R_2$ and $R_3$ together form a 3, 4, 5, 6 or 7 membered saturated or partially-unsaturated carbocyclic ring or a 3, 4, 5, 6, 7 or 8 membered saturated or partially unsaturated heterocyclic ring containing one or more heteroatoms selected from O, S and N;

wherein said carbocyclic ring or said heterocyclic ring when partially unsaturated or aromatic is optionally fused to an aryl ring.

According to a further aspect of the invention there is provided for use in therapy a compound of formula (I) wherein $R_2$ is H or alkyl, or a pharmaceutically acceptable salt or prodrug thereof.

The present invention may be employed in respect of a human or animal subject, more preferably a mammal, more preferably a human subject.

The disorders of particular interest are Parkinson's disease, drug-induced Parkinsonism, post-encephalitic Parkinsonism, Parkinsonism induced by poisoning (for example MPTP, manganese, carbon monoxide) and post-traumatic Parkinson's disease (punch-drunk syndrome).

Other movement disorders in which the therapy may be of benefit include progressive supernuclear palsy, Huntingtons disease, multiple system atrophy, corticobasal degeneration, Wilsons disease, Hallerrorden-Spatz disease, progressive pallidal atrophy, Dopa-responsive dystonia-Parkinsonism, spasticity, Alzheimer's disease or other disorders of the basal ganglia which result in abnormal movement or posture.

A further example of a disorder in which the blocking of purine receptors may be beneficial is depression.

The compound of formula (I) may be used or administered in combination with one or more additional drugs useful in the treatment of movement disorders, such as L-DOPA, the components being in the same formulation or in separate formulations for administration simultaneously or sequentially.

The present invention may also be effective in treating Parkinson's with on-off phenomena; Parkinson's with freezing (end of dose deterioration); and Parkinson's with prominent dyskinesias.

According to a further aspect of the invention, there is provided a compound of formula (I), or a pharmaceutically acceptable salt or prodrug thereof, other than:

(i) compounds in which $R_2$ or $R_3$ is selected from phenyl or substituted phenyl and $R_1$ and $R_5$ to $R_9$ are selected from hydrogen;

(ii) compounds in which $R_2$ or $R_3$ is selected from phenyl or substituted phenyl and one or two of $R_5$ to $R_9$ is selected from Cl, Br, methoxy and $NH_2$;

(iii) compounds in which $R_2$ or $R_3$ is methyl or isopropyl and $R_4$ and $R_9$ are $CF_3$;

(iv) compounds in which $R_2$ or $R_3$ is methyl or ethyl and one or two of $R_5$ to $R_9$ is selected from $NH_2$, Cl, F, methoxy, hydroxy and $OC(O)NEt_2$;

(v) compounds in which $R_2$ or $R_3$ is methyl, ethyl, n-butyl, t-butyl, 2-phenylethenyl, 1-nitroethyl or 1-aminoethyl and $R_5$ to $R_9$ are selected from hydrogen;

(vi) compounds in which $R_2$ or $R_3$ is methyl or t-butyl and $R_7$ and $R_9$ are methyl;

(vii) compounds in which $R_2$ or $R_3$ is selected from $CO_2Et$, $C(NH)OEt$ and $CF_3$ and four or five of $R_5$ to $R_9$ are selected from hydrogen;

(viii) compounds in which $R_2$ or $R_3$ is acyclic $C_1$ to $C_5$ alkyl substituted by phenyl or by an N-containing heterocycle or by a mono- or di-alkyl amino group or by a (dialkylamino)alkoxy group;

(ix) compounds in which $R_2$ or $R_3$ is pyridyl, indole, pyrimidine, piperidine, piperazine, pyrrolidine, 2-pyridyl-N-oxide;

(x) compounds in which $R_4$ is thienyl and $R_1$ to $R_3$ and $R_5$ to $R_9$ are hydrogen;

(xi) compounds in which $R_2$ and $R_3$ together form a cyclohexyl group, a 2-cyclohexenyl group or an N-methyl-4-piperidyl group and $R_7$ is selected from H, Cl, methyl or methoxy;

(xii) compounds in which $R_1$ and either $R_2$ or $R_3$ together form an oxygen-containing saturated heterocyclic ring;

(xiii) compounds in which $R_1$ and $R_2$ and $R_3$ together form a 5-membered oxygen-containing partially unsaturated or aromatic heterocyclic ring; and (xiv) compounds in which $R_1$ to $R_3$ and $R_5$ to $R_8$ are hydrogen and $R_4$ and $R_9$ are $CF_3$.

In an alternative embodiment of the invention, there is provided a compound of formula (I), or a pharmaceutically acceptable salt or prodrug thereof, other than:

compounds in which $R_2$ or $R_3$ is selected from phenyl or substituted phenyl;

(ii) compounds in which $R_2$ or $R_3$ is acyclic saturated alkyl and $R_4$ and $R_9$ are $CF_3$;

(iii) compounds in which $R_2$ or $R_3$ is selected from methyl, ethyl, n-butyl, t-butyl, 2-phenylethenyl, 1-nitroethyl, 1-aminoethyl, $CO_2Et$, C(NH)OEt and $CF_3$;

(iv) compounds in which $R_2$ or $R_3$ is alkyl substituted by phenyl or by an N-containing heterocycle or by a mono or di-alkyl amino group or by a (dialkylamino)alkoxy group;

(v) compounds in which $R_2$ or $R_3$ is a heterocyclic ring in which the ring atoms are selected only from carbon and nitrogen;

(vi) compounds in which $R_4$ is thienyl;

(vii) compounds in which $R_2$ and $R_3$ together form a cyclohexyl group, a 2-cyclohexenyl group or an N-methyl-4-piperidyl group;

(viii) compounds in which $R_1$ and $R_2$ and/or $R_3$ together form an oxygen-containing heterocyclic ring; and (ix) compounds in which $R_1$ to $R_3$ are hydrogen and $R_4$ and $R_9$ are $CF_3$.

In a further alternative embodiment of the invention, there is provided a compound of formula (I), or a pharmaceutically acceptable salt or prodrug thereof, other than:

(i) compounds in which $R_2$ or $R_3$ is selected from carbocyclic aromatic groups;

(ii) compounds in which $R_2$ or $R_3$ is selected from acyclic alkyl, $CO_2$(alkyl) and C(NH)O(alkyl);

(iii) compounds in which $R_2$ or $R_3$ is alkyl substituted by aryl or by a saturated N-containing heterocycle or by a mono- or di-alkyl amino group or by a (dialkylamino)alkoxy group;

(iv) compounds in which $R_2$ or $R_3$ is an N-containing heterocyclic ring;

(v) compounds in which $R_4$ is an S-containing heterocyclic ring;

(vi) compounds in which $R_2$ and $R_3$ together form a 6-membered carbocyclic group or a 6-membered N-containing heterocyclic ring;

(vii) compounds in which $R_1$ and $R_2$ and/or $R_3$ together form an oxygen-containing heterocyclic ring; and (viii) compounds in which $R_1$ to $R_3$ are hydrogen.

According to a further aspect of the invention, there is provided a compound of formula (I), or a pharmaceutically acceptable salt or prodrug thereof, wherein:

(i) $R_3$ is a 5 or 6 membered unbridged saturated, partially unsaturated or aromatic heterocyclic ring in which the one or more heteroatoms are selected only from O and S; or (ii) $R_3$ is a 3, 4, 5, 6 or 7 membered carbocyclic ring; or (iii) $R_2$ and $R_3$ together form a 3, 4, 5 or 7 membered saturated or partially-unsaturated carbocyclic ring, or a 4, 5, 6 or 7 membered saturated or partially unsaturated heterocyclic ring in which the one or more heteroatoms are selected only from O and S, or a 4, 5 or 7 membered saturated or partially unsaturated heterocyclic ring containing one or more heteroatoms selected from N, and preferably a 3, 4, 5 or 7 membered saturated or partially-unsaturated carbocyclic ring or a 4, 5, 6 or 7 membered saturated or partially unsaturated heterocyclic ring in which the one or more heteroatoms are selected only from O and S; or (iv) $R_1$ is $C_1$ to $C_4$ acyclic alkyl and $R_3$ is aryl (including heteroaryl) or $C_3$ to $C_7$ cycloalkyl; or (v) $R_1$ is $C_1$ to $C_4$ acyclic alkyl and $R_2$ and $R_3$ together form a 3, 4, 5, 6 or 7 membered saturated or partially-unsaturated carbocyclic ring or a 3, 4, 5, 6, 7 or 8 membered saturated or partially unsaturated heterocyclic ring containing one or more heteroatoms selected from O, S and N, wherein said carbocyclic ring or said heterocyclic ring when partially unsaturated or aromatic is optionally fused to an aryl ring.

According to a further aspect of the invention there is provided a compound of formula (I) wherein $R_2$ is H or alkyl, or a pharmaceutically acceptable salt or prodrug thereof.

The invention further relates to the compounds disclosed herein.

According to a further aspect of the invention, there is provided a method of preparing the novel compounds of formula (I), and pharmaceutically acceptable salts and prodrugs thereof. Compounds of formula (I) may be prepared by conventional synthetic methods such as those illustrated in Reaction Scheme 1.

Reaction Scheme 1

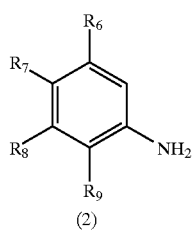
(2)

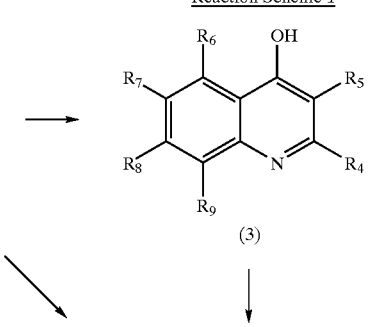
(3)

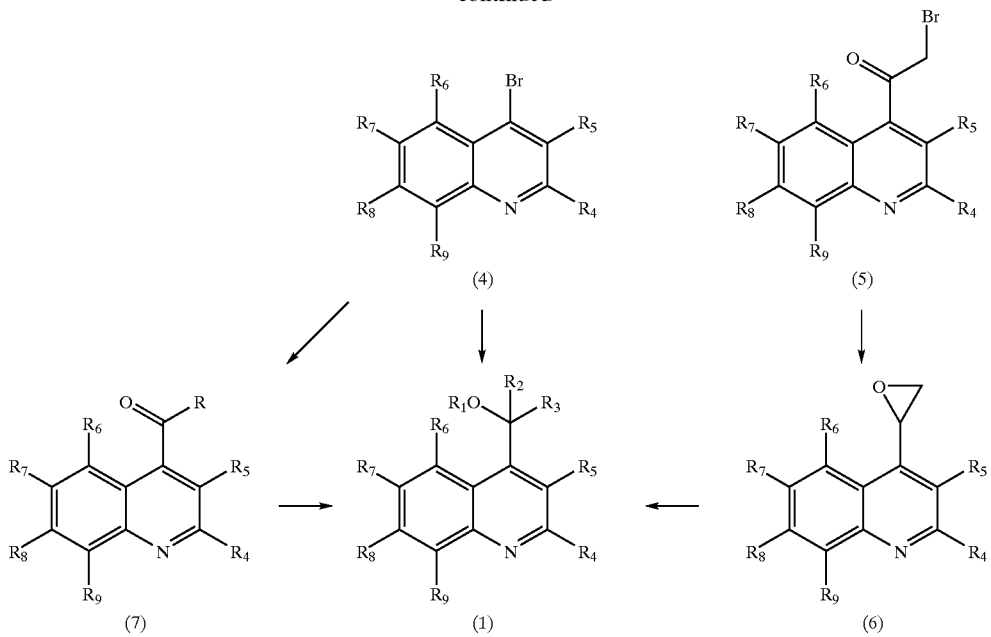

Compounds of formula (1) where $R_1$ is H and $R_2$ to $R_9$ are as defined above, are prepared by standard methods from 4-bromoquinolines (4) for example by initial reaction with a metallating reagent such as BuLi and reacting the subsequent metallated carbanion with a carbonyl-containing compound such as an aldehyde ($R_2CHO$) or a ketone ($R_2COR_3$). Alternatively compounds of formula (1) where $R_1$ is H are prepared from carbonyl-containing compounds (7) where R is $R_2$ or alkoxy, either by reduction with a standard reducing agent such as $NaBH_4$ or by addition of a carbanionic species such as an alkyl or aryl lithium reagent or a Grignard reagent. When compounds (7), where R is alkoxy are treated with a carbanionic species as above, the reaction conditions may be controlled by standard methods to preferentially give compounds (1) where $R_2=R_3$, or compounds (1) where $R_2$ and $R_3$ are different. Carbonyl-containing compounds (7) may be prepared from 4-bromoquinolines (4) by metallation as described above, followed by reaction with a carbonyl-containing compound such as an ester ($RCO_2$alkyl) to give a ketone (7) where R is alkyl or aryl, a lactone to give a ketone (7) where R is hydroxyalkyl, an alkyl chloroformate or dialkyl carbonate to give an ester (7) where R is alkoxy, or a dialkyl formamide (eg DMF) to give an aldehyde (7) where R is H.

Compounds of formula (1) where $R_1$ is alkyl are prepared by standard methods from compounds of formula (1) where $R_1$ is H for example by alkylation with an alkyl halide in the presence of a suitable base such as NaH.

Compounds of formula (1) where $R_1$ is H and either $R_2$ or $R_3$ is substituted alkyl may also be prepared from epoxides (6) by reaction with an appropriate nucleophile. Treatment for example with an amine, alcohol or fluoride may lead to compounds of formula (1) where $R_1$ is H and either $R_2$ or $R_3$ is an alkyl group substituted in the β-position by an amine group, an ether group or a fluoro group. Epoxides (6) are either known in the literature or may be prepared from bromoketones (5) by standard literature methods such as, for example treatment with a reducing agent such as $NaBH_4$. Bromoketones (5) are either known in the literature or are prepared from suitably substituted ketones (7) by standard methods such as α-bromination.

Compounds of formula (1) where $R_1$ together with its attached oxygen atom and together with $R_2$ and $R_3$ forms a partially unsaturated or aromatic 5-membered, oxygen-containing heterocyclic ring, such as for example a furan, may be prepared from 4-bromoquinolines (4) by standard methods such as a palladium-catalysed vinyl or aryl coupling reaction with an appropriately activated heteroaryl derivative such as an arylboronic acid. This methodology may be used to prepare compounds of formula (1) where $R_1$ together with it's attached oxygen atom and together with $R_2$ and $R_3$, form a variety of unsaturated 5-membered, oxygen-containing heterocyclic rings such as furans, benzofurans, oxazoles, benzoxazoles, isoxazoles, benzisoxazoles and oxadiazoles.

Compounds of formula (1) where $R_1$ together with its oxygen atom and together with $R_2$ or $R_3$ forms a saturated or partially unsaturated 4, 5, 6, 7 or 8-membered oxygen-containing heterocyclic ring are prepared from compounds of formula (1) where $R_1$ is H and $R_2$ is an alkyl group substituted in an appropriate position with a suitable leaving group such as a tosylate, mesylate or halogen, by treatment with an appropriate base such as triethylamine.

Compounds of formula (1) where $R_2$ is an alkyl group substituted with a leaving group may be prepared from compounds of formula (1) where $R_2$ is an alkyl group substituted by a hydroxy group for example by treatment with p-toluenesulphonyl chloride or methanesulphonyl chloride in the presence of a suitable base such as triethylamine. In favourable cases conversion of the hydroxy group to a leaving group may result in spontaneous cyclisation to a compound of formula (1) where $R_1$ together with it's oxygen atom and together with $R_2$ forms a saturated 4, 5, 6, 7, or 8-membered oxygen-containing heterocyclic ring.

Compounds of formula (1) where $R_1$ is H and $R_2$ is an alkyl group substituted in an appropriate position with a hydroxy group are prepared from ketones (7) where R is a hydroxyalkyl group by standard methods such as reduction with. for example, $NaBH_4$.

Compounds of formula (1) where $R_4$ an amino, alkylamino or arylamino ($NR_{10}R_{11}$), alkoxy, aryloxy, alkylthio or arylthio ($SR_{10}$) or cyano group are prepared from compounds of formula (1) where $R_4$ is a halogen, preferably bromine, by standard methods such as reaction with an appropriate nucleophilic reagent such as ammonia, an alkylamine, arylamine, alkoxide, aryloxide, alkylthiolate, arylthiolate or cyanide.

Compounds of formula (1) where $R_4$ is an amino ($NH_2$) group may also be prepared from compounds of formula (1) where $R_4$ is a halogen in two steps by reaction with an amine which is substituted with a suitable protecting group such as a benzyl or substituted benzyl group, followed by a deprotection step where the amine protecting group is removed by standard methodology such as hydrogenation or treatment with strong acid.

Compounds of formula (1) where $R_4$ is an alkylamino or dialkylamino group may also be prepared from compounds of formula (1), where $R_4$ is an unsubstituted amino or mono-substituted amino group, by standard methods such as alkylation or dialkylation by reaction with, for example an alkyl halide in the presence of a suitable base, or alternatively by reductive alkylation by reaction with a suitable aldehyde or ketone in the presence of a suitable reducing agent such as $NaCNBH_3$, or alternatively by acylation with a suitable acylating agent such as an acid chloride or anhydride, followed by reduction of the subsequent amide using a standard reagent such as $BH_3$. Compounds of formula (1) where $R_4$ is an amino, monoalkylamino or monoarylamino group ($NHR_{10}$) may be converted by standard methods to compounds of formula (1) where $R_4$ is $NR_{10}COR_{11}$, $NR_{10}CO_2R_{11}$, $NR_{10}CONR_{11}R_{12}$, or $NR_{10}SO_2R_{11}$ for example by treatment with an acid chloride ($R_{11}COCl$), chloroformate ($ClCO_2R_{11}$), isocyanate ($R_{11}NCO$), chloroformamide ($ClCONR_{11}R_{12}$) or sulphonyl chloride ($ClSO_2R_{11}$) or by using one of a large variety of alternative reagents known to those skilled in the art.

Compounds of formula (1) where $R_4$ is a substituted hydrazine group such as $NR_{10}NR_{11}COR_{12}$, $NR_{10}NR_{11}CO_2R_{12}$, $NR_{10}NR_{11}CONR_{12}R_{13}$ or $NR_{10}NR_{11}SO_2R_{12}$ may be prepared from a compound of formula (1) where $R_4$ is halogen by reaction with a suitably substituted hydrazine derivative or alternatively prepared from a compound of formula (1) where $R_4$ is $NR_{10}NHR_{11}$, by reaction with, for example an acid chloride ($R_{12}COCl$), chloroformate ($ClCO_2R_{12}$), isocyanate ($R_{12}NCO$), chloroformamide ($ClCONR_{12}R_{13}$) or sulphonyl chloride ($ClSO_2R_{12}$). Compounds of formula (1) where $R_4$ is $NR_{10}NHR_{11}$ may be prepared from compounds of formula (1) where $R_4$ is a halogen by treatment with hydrazine or a suitably substituted hydrazine derivative.

Compounds of formula (1) where $R_4$ is a sulphoxide ($SOR_{10}$) or sulphone ($SO_2R_{10}$) group are prepared from a compound of formula (1) where $R_4$ is a thioether ($SR_{10}$) by standard methods such as by treatment with a suitable oxidising agent such as m-chloroperbenzoic acid or alternative oxidising agent known to those skilled in the art to permit selective mono- or di-oxygenation.

Compounds of formula (1) where $R_4$ is hydroxy (OH) are prepared from compounds of formula (1) where $R_4$ is a halogen, preferably bromine, by standard methods such as hydrolysis with, for example aqueous acid.

Compounds of formula (1) where $R_4$ is an alkoxy, acyloxy ($OCOR_{10}$) or carbamate ($OCONR_{10}R_{11}$) group may be prepared from a compound of formula (1) where $R_4$ is a hydroxy group by standard methods such as alkylation or acylation or by reaction with an appropriate isocyanate.

Compounds of formula (1) where $R_4$ is an ester ($CO_2R_{10}$), aldehyde (CHO) or amide ($CONR_{10}R_{11}$) are prepared from compounds of formula (1) where $R_4$ is a halogen, preferably bromine, by standard methods such as metallation with, for example BuLi to form a metallated carbanion, followed by reaction with, for example a chloroformate ($ClCO_2R_{10}$), dialkylformamide (for example DMF), isocyanate ($R_{10}NCO$) or chloroformamide ($ClCONR_{12}R_{13}$).

Further modification of a compound of formula (1) where $R_4$ is an ester, amide or aldehyde can lead, by using standard literature methods, to compounds of formula (1) where $R_4$ is, for example a carboxylic acid, hydroxyalkyl, aminoalkyl, cyano, amidine, carboxylic hydrazide ($CONR_{10}NR_{11}R_{12}$) or oxime ($CR_{10}NOR_{11}$) group.

Further modification of a compound of formula (1) where $R_4$ is an ester, amide, hydrazide, amidine, aldehyde, cyanide or carboxylic acid can lead, by using standard literature methods, to compounds of formula (1) where $R_4$ is, for example a 5- or 6-membered heterocyclic ring such as an oxadiazole, thiadiazole, thiazole, oxazole, isoxazole, pyrazole, triazole, tetrazole, imidazole or pyrimidine.

4-Bromoquinolines (4) are either known in the literature or may be prepared from 4-hydroxyquinolines (3) by standard literature methods such as treatment with $POBr_3$. 4-Bromoquinolines (4) where $R_4$ is also a bromine atom are either known in the literature or are prepared directly from anilines (2) by treatment with, for example malonic acid or a suitably substituted malonic acid in the presence of $POBr_3$. 4-Bromoquinolines (4) where $R_4$ is also a bromine atom may also be prepared from known 4-hydroxyquinolines (3) where $R_4$ is also hydroxy, by treatment with $POBr_3$. 4-Hydroxyquinolines (3) are either known in the literature or may be prepared from anilines (2) by standard literature methods such as by reaction with a suitably substituted acetoacetate ester derivative in the presence of a suitable acid catalyst or dehydrating agent such as polyphosphoric acid. Anilines (2) are either commercially available, are known in the literature or may be prepared by standard literature methods.

Synthetic preparation of some of the compounds of formula (1) where $R_1$–$R_9$ are as defined above, may require the use of protecting groups to avoid certain functional groups interfering in the normal course of a reaction. The protecting groups used in the preparation of the compounds of formula (1) may be selected from a range of protecting groups commonly used in organic synthesis. This may include, for example the protection of amines with benzyl, substituted benzyl, diphenylmethyl or butoxycarbonyl groups or as a nitro group, the protection of alcohols with, for example benzyl, substituted benzyl, t-butyl or trialkylsilyl groups, and the protection of ketones as ketals or thioketals. In all cases deprotection of these functional groups is carried out by standard literature procedures known to those skilled in the art.

According to a further aspect of the invention, there is provided a pharmaceutical composition comprising a compound of formula (I), or a pharmaceutically acceptable salt or prodrug thereof, in combination with a pharmaceutically acceptable carrier or excipient and a method of making such a composition comprising combining a compound of formula (I), or a pharmaceutically acceptable salt or prodrug thereof, with a pharmaceutically acceptable carrier or excipient.

The pharmaceutical compositions employed in the present invention comprise a compound of formula (I), or a pharmaceutically acceptable salt or prodrug thereof, and may also contain other therapeutic ingredients known to those skilled in the art.

Any suitable route of administration may be employed for providing the patient with an effective dosage of a compound of formula (I). For example, oral, rectal, parenteral (intravenous, intramuscular), transdermal, subcutaneous, and the like may be employed. Dosage forms include tablets, troches, dispersions, suspensions, solutions, capsules, patches, and the like. The most suitable route in any given case will depend on the severity of the condition being treated. The most preferred route of administration according to the present invention is the oral route. The compositions may be conveniently presented in unit dosage form and prepared by any of the methods well known in the art of pharmacy.

In practical use, a compound of formula (I), or a pharmaceutically acceptable salt or prodrug thereof, can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (e.g. intravenous). In preparing the compositions for oral dosage form, any of the usual pharmaceutical media may be employed as carriers, such as, for example, water, glycols, oils, alcohols, flavouring agents, preservatives, colouring agents, and the like in the case of oral liquid preparations (such as suspensions, solutions and elixirs) or aerosols; or carriers such as starches, sugars, micro-crystalline cellulose, diluents, granulating agents, lubricants, binders, disintegrating agents, and the like may be used in the case of oral solid preparations such as, for example, powders, capsules and tablets, with the solid oral preparations being preferred over the liquid preparations. The most preferred solid oral preparation is tablets.

Because of their ease of administration, tablets and capsules represent the most advantageous oral dosage unit form, in which case solid pharmaceutical carriers are employed. If desired, tablets may be coated by standard aqueous or non-aqueous techniques.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; 3,630,200; 4,008,719; 4,687,660; and 4,769,027, the disclosures of which are hereby incorporated by reference.

Pharmaceutical compositions employed in the present invention suitable for oral administration may be presented as discrete units such as capsules, cachets, or tablets, or aerosol sprays each containing a predetermined amount of the active ingredient as a powder or granules, a solution or a suspension in an aqueous liquid, an oil-in-water emulsion, or a water-in-oil liquid emulsion. Such compositions may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or moulding, optionally with one or more accessory ingredients. Compressed tablets may be prepared by compressing in a suitable machine the active ingredient in a free-flowing form such as powder or granules, optionally mixed with a binder, a lubricant, an inert diluent, and/or a surface active or dispersing agent. Moulded tablets may be made by moulding in a suitable machine a mixture of the powdered compound moistened with an inert liquid diluent.

The invention is further defined by reference to the following examples. It will be apparent to those skilled in the art that many modifications, both to materials and methods, may be practised without departing from the purpose and interest of this invention.

EXAMPLES

Synthetic Examples

Method A

Example 1

2,8- Bis(trinfluoromethyl)-α-phenyl-4-quinolinemethanol

To a stirred solution of 2,8-bis(trifluoromethyl)-4-bromoquinoline (500 mg, 1.45 mmol) in dry ether (10 mL) at −78° C. under argon was added n-BuLi (2.5-M, 0.64 mL, 1.1 eq). After 15 min benzaldehyde (0.15 mL, 1 eq) was added dropwise, the mixture stirred for 1 h, water (10 mL) was added, the mixture allowed to warm slowly to room temperature and extracted with ether (3×20 mL). The combined extracts were dried ($MgSO_4$), concentrated in vacuo and the residue purified by chromatography $SiO_2$; heptane-EtOAc (3:1) to give the title compound (193 mg, 36%) as a pale-yellow solid: mp 151–152° C.; IR $v_{max}$ (Nujol)/cm$^{-1}$ 3278, 2955, 1456, 1309, 1142, 1109 and 844; NMR $δ_H$ (400 MHz, $CDCl_3$) 2.49 (1H, d, J 3.6 Hz), 6.53 (1H, d, J 3.4 Hz), 7.33–7.40 (5H, m), 7.57–7.61 (1H, m), 8.09–8.18 (2H, m) and 8.27 (1H, s); Anal. Calcd for $C_{18}H_{11}F_6NO$: C, 58.23; H, 2.99; N, 3.77. Found: C, 57.97; H, 3.04; N, 3.69.

The following compounds (Examples 2–68) were synthesised using Method A from the appropriately substituted 4-bromoquinoline and the appropriate carbonyl compound:

Example 2

2,8-Bis(trifluoromethyl)-α-(2-thienyl)-4-quinolinemethanol

Isolated as a white crystalline solid, (217 mg, 85%): IR $v_{max}$ (Nujol)/cm$^{-1}$ 3252, 2925, 2854, 1604, 1586, 1462, 1432, 1377, 1309, 1270, 1215, 1172, 1142, 1109, 1076, 772 and 711; NMR $δ_H$ (400 MHz, $CDCl_3$) 2.67 (1H, d, J 3.8 Hz), 6.77 (1H, d, J 3.8 Hz), 6.90 (1H, d, J 3.4 Hz), 6.95 (1H, m), 7.33 (1H, m), 7.65 (1H, t, J 8 Hz), 8.13 (1H, d, J 7.2 Hz), 8.19 (1H, d, 8.6 Hz) and 8.27 (1H, s).

Example 3

2,8-Bis(trifluoromethyl)-α-(3-thienyl)-4-quinolinemethanol

Isolated as a white crystalline solid,(152 mg, 55%): IR $v_{max}$(Nujol)/cm$^{-1}$ 3277, 2955, 2924, 2854, 1602, 1586, 1463, 1431, 1376, 1309, 1272, 1214, 1187, 1171, 1141, 1127, 1109, 1078, 840, 772 and 675; NMR $δ_H$ (400 MHz, $CDCl_3$) 2.52 (1H, d, J 3.8 Hz), 6.62 (1H, d, J 3.8 Hz), 7.00 (1H, m), 7.18 (1H, d, 2.5 Hz), 7.33 (1H, m), 7.63 (1H, t, J 7.9 Hz), 8.12 (1H, d, J 7.2 Hz), 8.16 (1H, d, J 8.7 Hz) and 8.22 (1H, s).

Example 4

2,8-Bis(trifluoromethyl)-α-(2-furyl)-4-quinolinemethanol

Isolated as a white crystalline solid, (134 mg, 51%): IR $v_{max}$ (Nujol)/cm$^{-1}$ 3264, 2924, 2854, 1605, 1586, 1463, 1433, 1376, 1310, 1272, 1215, 1187, 1139, 1110, 1080, 1013, 837, 749 and 673; NMR $\delta_H$ (400 MHz, CDCl$_3$) 2.71 (1H, d, J 3.8 Hz), 6.10 (1H, d, J 3.2 Hz), 6.33 (1H, m), 6.59 (1H, d, J 3.8 Hz), 7.42 (1H, m), 7.67 (1H, t, J 7.9 Hz), 8.15 (2H, m) and 8.22 (1H, s).

Example 5

2,8-Bis(trifluoromethyl)-α-(3-furyl)-4-quinolinemethanol

Isolated as a white crystalline solid, (114 mg, 44%): IR $\nu_{max}$ (Nujol)/cm$^{-1}$ 3250, 2924, 2854, 1603, 1586, 1461, 1432, 1376, 1310, 1273, 1215, 1191, 1152, 1140, 1109, 1078, 1029, 873, 838, 802, 775, 731 and 674; NMR $\delta_H$ (400 MHz, CDCl$_3$) 2.44 (1H, d, J 3.9 Hz), 6.33 (1H, s), 6.53 (1H, d, J 3.9 Hz), 7.34 (1H, s), 7.40 (1H, d, J 1.6 Hz), 7.67 (1H, t, J 7.9 Hz), 8.14 (1H, d, J 7.2 Hz), 8.20 (1H, s) and 8.21 (1H, m).

Example 6

2,8-Bis(trinfluoromethyl)-α-benzyl-4-quinolinemethanol

Isolated as a waxy solid, (163 mg, 58%): IR $\nu_{max}$ (Nujol)/cm$^{-1}$ 3627, 2955, 2924, 2854, 1608, 1585, 1456, 1371, 1308, 1283, 1199, 1179, 1137, 1110, 1086, 1066, 932, 901, 764, 748 and 700; NMR $\delta_H$ (400 MHz, CDCl$_3$) 2.34 (1H, d, J 3.1 Hz), 2.98 (1H, dd, J 14, 9.2 Hz), 3.26 (1H, dd, J 14, 3.4 Hz), 5.71 (1H, ddd, J 9, 3.4, 3.2 Hz), 7.28 (2H, m), 7.35 (3H, m), 7.75 (1H, t, J 7.9 Hz), 8.05 (1H, s), 8.18 (1H, d, J 7.2 Hz) and 8.31 (1H, d, J 8.5 Hz).

Example 7

2,8-Bis(trifluoromethyl)-α-clohexyl-4-quinolinemethanol

Isolated as a colourless oil, (141 mg, 51%): IR $\nu_{max}$ (Nujol)/cm$^{-1}$ 3426, 2932, 2857, 1601, 1505, 1516, 1452, 1430, 1309, 1211, 1189, 1144 and 1110; NMR $\delta_H$ (400 MHz, CDCl$_3$) 1.09–1.31 (5H, m), 1.50–1.53 (1H, m), 1.67–1.81 (5H, m), 2.19 (1H, d, J 4.0 Hz), 5.28–5.30 (1H, m), 7.72 (1H, t, J 8.0 Hz), 7.95 (1H, s), 8.16 (1H, d, J 8.0 Hz) and 8.31 (1H, d, J 8.0 Hz).

Example 8

Bis(2,8-bis(trifluoromethyl)-4-quinolinyl)methanol

Isolated as an off-white solid, (226 mg, 52%): mp 198–199° C.; IR $\nu_{max}$ (Nujol)/cm$^{-1}$ 3444, 2924, 1306, 1167, 1110 and 768; NMR $\delta_H$ (400 MHz, CDCl$_3$) 3.11 (1H, d, J 5.0 Hz), 7.31 (1H, d, J 4.4 Hz), 7.74–7.78 (4H, m) and 8.19–8.25 (4H, m).

Example 9

2,8-Bis(trifluoromethyl)-α-phenyl-4-quinolineethanol

Isolated as a white solid, (121 mg, 43%): m.p. 111–112° C.; IR $\nu_{max}$ (Nujol)/cm$^{-1}$ 3592, 2955, 2924, 2854, 1602, 1592, 1584, 1456, 1448, 1375, 1368, 1328, 1308, 1272, 1223, 1194, 1166, 1121, 1116, 1057 and 1025; NMR $\delta_H$ (400 MHz, CDCl$_3$) 2.15 (3H, s), 2.46 (1H, s), 7.28–7.35 (5H, m), 7.41 (1H, t, J 8.0 Hz), 8.02 (1H, d, J 7 Hz), 8.05 (1H, d, J 8.0 Hz) and 8.28 (1H, s); Anal. Calcd for C$_{19}$H$_{13}$F$_6$NO: C, 59.23; H, 3.40; N, 3.63. Found: C, 59.13; H, 3.33; N, 3.58.

Example 10

1-(2,8-Bis(tnfluoromethyl)-4-quinolinyl)-1-indanol

Isolated as a pale yellow solid, (216 mg, 75%): IR $\nu_{max}$ (Nujol)/cm$^{-1}$ 3539, 2921, 2854, 1597, 1588, 1459, 1428, 1377, 1310, 1276, 1184, 1138, 1115, 1077, 768, 745 and 703; NMR $\delta_H$ (400 MHz, CDCl$_3$) 2.33 (1H, s), 2.64 (1H, m), 2.81 (1H, m), 3.13 (1H, m), 3.39 (1H, m), 6.97 (1H, d, J 7.1 Hz), 7.23 (1H, d, J 7.3 Hz), 7.42 (1H, m), 7.47 (2H, m), 7.95 (1H, m) and 8.07 (2H, m).

Example 11

1-(2,8-Bis(trifluoromethyl)-4-quinolinyl)-1,2,3,4-tetrabydro-1-naphthol

Isolated as a cream solid, (105 mg, 26%): mp 128.8–129.4° C.; IR $\nu_{max}$ (Nujol)/cm$^{-1}$ 3428, 2924, 2854, 1458, 1309, 1152 and 1112; NMR $\delta_H$ (400 MHz, CDCl$_3$) 1.99–2.06 (1H, m), 2.15–2.42 (4H, m), 3.07–3.11 (2H, m), 6.73 (1H, d, J 7.4 Hz), 7.03 (1H, t, J 7.5 Hz), 7.26 (1H, t, J 8.0 Hz), 7.32 (1H, d, J 7.1 Hz), 7.37 (1H, t, J 8.1 Hz), 7.55 (1H, d, J 8.7 Hz), 8.01 (1H, d, J 7.8 Hz) and 8.58 (1H, s); Anal. Calcd for C$_{21}$H$_{15}$F$_6$NO.0.2 H$_2$O: C, 60.79; H, 3.74; N, 3.38. Found: C, 60.82; H, 3.75; N, 3.37.

Example 12

1-(2,8-Bis(trifluorometbyl)-4-quinolinyl)-2-indanol

Isolated as an off-white solid, (52 mg, 9%): mp 136–137° C.; IR $\nu_{max}$ (Nujol)/cm$^{-1}$ 3530, 2922, 1599, 1462, 1310, 1177 and 758; NMR $\delta_H$ (400 MHz, CDCl$_3$) 2.48 (1H, s), 3.45 (2H, d, J 17.5 Hz), 3.90 (2H, d, J 17.1 Hz), 7.34–7.35 (3H, m), 7.60 (1H, t, J 8.6 Hz), 8.13 (1H, d, J 7.5 Hz), 8.16 (1H, d, J 8.4 Hz) and 8.23 (1H, s); Anal. Calcd for C$_{20}$H$_{13}$F$_6$NO: C, 60.46; H, 3.30; N, 3.52. Found: C, 60.25; H, 3.33; N, 3.36.

Example 13

1-(2,8-Bis(trifluoromethyl)-4-quinolinyl)cyclobexanol

Isolated as a crystalline solid, (130 mg, 49%): m.p. 77–78° C.; IR $\nu$(Nujol)/cm$^{-1}$ 3610, 2924, 2855, 1596, 1586, 1513, 1455, 1375, 1343, 1310, 1284, 1222, 1181, 1156, 1136, 1121 and 1092; NMR $\delta_H$ (400 MHz, CDCl$_3$) 1.37–1.40 (1H, m), 1.78–2.08 (8H, m), 2.19–2.22 (2H, m), 7.68 (1H, t, J 8.0 Hz), 7.86 (1H, s), 8.13 (1H, d, J 7.0 Hz) and 9.18 (1H, d, J 8.0 Hz).

Example 14

4-(2,8-Bis(trifluoromethyl)-4-quinolinyl)tetrabydrothiopyran-4ol

Isolated as a viscous yellow oil, (92 mg, 33%): NMR $\delta_H$ (400 MHz, CDCl$_3$) 2.30–2.40 (2H, m), 2.50–2.65 (4H, m), 3.38 (1H, t, J 13.0 Hz), 7.73 (1H, d, J 8.0 Hz), 7.90 (1H, s), 8.15 (1H, d, J 7.0 Hz) and 9.12 (1H, d, J 9.0 Hz).

Example 15

2,8-Bis(trinfluoromethyl)-3-methyl-α-phenyl-4-quinolinemethanol

Isolated as a cream solid, (103 mg, 27%): mp 138.5–140° C.; IR $\nu_{max}$ (Nujol)/cm$^{-1}$ 3529, 2925, 2854, 1583, 1495, 1462, 1310, 1197, 1140, 1128, 778, 752; NMR $\delta_H$ (400

MHz, CDCl₃) 2.67 (3H, s), 2.75 (1H, d, J 4.7 Hz), 6.82 (1H, d, J 4.1 Hz), 7.26–7.36 (6H, m), 7.48–7.52 (1H, dd, J 8.0, 8.1 Hz), 8.02 (1H, d, J 7.1 Hz), 8.44 (1H, d, J 8.4 Hz) ; Anal. Calcd for $C_{19}H_{13}F_6NO$: C, 59.23; H, 3.40; N, 3.63. Found: C, 59.29; H, 3.47; N, 3.50.

Example 16

2,8-Bis(trifluoromethyl)-3-methyl-α-(2-thienyl)-4-quinolinemethanol

Isolated as a cream solid, (158 mg, 40%): mp 125.1–125.8° C.; IR $\nu_{max}$ (Nujol)/cm⁻¹ 3546, 3092, 2924, 2854, 1582, 1496, 1463, 1414, 1366, 1309, 1135, 1092, 781; NMR $\delta_H$ (400 MHz, CDCl₃) 2.65 (3H, s), 2.68 (1H, d, J 4.6 Hz), 6.76 (1H, d, J 4.0 Hz), 6.90 (1H, d, J 5.0 Hz), 7.01–7.04 (1H, m), 7.26–7.34 (1H, m), 7.53 (1H, t, J 8.1 Hz), 8.01 (1H, d, J 7.5 Hz), 8.55 (1H, d, J 8.9 Hz) .

Example 17

α-(3-Benzyloxymethylphenyl)-2,8-bis(trifluoromethyl)-4-quinolinemethanol

Isolated as a viscous oil, (194 mg, 34%): NMR $\delta_H$ (400 MHz, CDCl₃) 4.51 (2H, s), 4.54 (2H, s) 6.42 (1H, br s), 7.20–7.35 (6H, m), 7.50 (1H, t, J 8.0 Hz), 8.07 (2H, d, J 8.0 Hz) and 8.22 (1H, s).

Example 18

2,8-Bis(trifluoromethyl)-α-(2-chlorophenyl)-4-quinolinemethanol

Isolated as a white solid, (300 mg, 87%): mp 147–148° C.; IR $\nu_{max}$ (Nujol)/cm⁻¹ 3266, 2925, 2845, 1606, 1589, 1517, 1464, 1440, 1377, 1308, 1271, 1212, 1196, 1146, 1108 and 1081; NMR $\delta_H$ (400 MHz, CDCl₃) 2.69 (1H, d, J 4.0 Hz), 6.98–7.00 (2H, m), 7.19 (1H, td J 7.5, 1.5 Hz), 7.30 (1H, td J 7.5, 1.5 Hz), 7.51 (1H, dd, J 6.5, 1.5 Hz), 7.63 (1H, t, J 8.0 Hz), 8.02 (1H, d, J 8.5 Hz), 8.12 (1H, d, J 7.0 Hz) and 8.20 (1H, s); Anal. Calcd for $C_{18}H_{10}ClF_6NO$: C, 53.29; H, 2.48; N, 3.45. Found: C, 53.02; H, 2.73; N, 3.32.

Example 19

2,8-Bis(trifluoromethyl)-α-(2-nitrophenyl)-4-quinolinemethanol

Isolated as a cream solid, (131 mg, 32%): IR $\nu_{max}$ (Nujol)/cm⁻¹ 3578, 2924, 2854, 1604, 1587, 1522, 1463, 1354, 1313, 1289, 1198, 1139 and 1109; NMR $\delta_H$ (400 MHz, CDCl₃) 3.41 (1H, d, J 4.5 Hz), 7.11 (1H, d, J 4.5 Hz), 7.14–7.17 (1H, m), 7.54–7.57 (2H, m), 7.63 (1H, t, J 8.0 Hz), 7.93 (1H, d, J 8.5 Hz) and 8.10–8.15 (3H, m).

Example 20

2,8-Bis(trifluoromethyl)-α-(2,6-dichlorophenyl)-4-quinolinemethanol

Isolated as a white solid, (306 mg, 70%): mp 151.2–151.7° C.; IR $\nu_{max}$ (Nujol)/cm⁻¹ 3400–3200, 2954, 2924, 2854, 1604, 1585, 1438, 1307, 1190, 1156, 1110, 1078 and 771; NMR $\delta_H$ (400 MHz, CDCl₃) 3.38 (1H, d, J 9.5 Hz), 7.17 (1H, d, J 9.1 Hz), 7.32 (1H, t, J 8.0 Hz), 7.42–7.44 (2H, m), 7.66 (1H, t, J 7.8 Hz), 7.88 (1H, s), 8.14 (1H, d, J 7.1 Hz) and 8.31 (1H, d, J 8.0 Hz) ; Anal. Calcd for $C_{18}H_7Cl_2F_6NO$: C, 49.12; H, 2.06; N, 3.18. Found: C, 49.22; H, 2.07; N, 3.18.

Example 21

2,8-Bis(trifluoromethyl)-α-(2-bromophenyl)-4-quinolinemethanol

Isolated as an off-white solid, (570 mg, 69%): mp 147–149° C.; IR $\nu_{max}$ (Nujol)/cm⁻¹ 3278, 2925, 1588, 1466, 1445, 1377, 1308, 1196, 1146, 1126 and 1108; NMR $\delta_H$ (400 MHz, CDCl₃) 2.71 (1H, d, J 4.0 Hz), 6.93–6.96 (2H, m), 7.20–7.26 (2H, m), 7.63 (1H, t, J 8.0 Hz), 7.68–7.69 (1H, m), 7.98 (1H, d, J 8.0 Hz), 8.12 (1H, d, J 7.0 Hz) and 8.19 (1H, m); Anal. Calcd for $C_{18}H_{10}BrF_6NO$: C, 48.03; H, 2.24; N, 3.11. Found: C, 48.17; H, 2.21; N, 3.13.

Example 22

2,8-Bis(trifluoromethyl)-α-(2-fluorophenyl)-4-quinolinemethanol

Isolated as a pale brown crystalline solid, (363 mg, 74%): mp 119.5–120.8° C.; IR $\nu_{max}$ (Nujol)/cm⁻¹ 3300–3200, 2925, 2854, 1606, 1584, 1493, 1458, 1306, 1154, 1108 and 762; NMR $\delta_H$ (400 MHz, CDCl₃) 2.59 (1H, d, J 4.0 Hz), 6.90 (1H, d, J 3.5 Hz), 7.05–7.17 (3H, m), 7.29–7.35 (1H, m), 7.63 (1H, t, J 7.9 Hz), 8.12 (2H, t, J 7.9 Hz) and 8.25 (1H, s); Anal. Calcd for $C_{18}H_{10}F_7NO \cdot 0.2 H_2O$: C, 55.03; H, 2.67; N, 3.57. Found: C, 55.18; H, 2.97; N, 3.38.

Example 23

2,8-Bis(trifluoromethyl-α-(2-methoxyphenyl)-4-quinolinemethanol

Isolated as a white crystalline solid, (37 mg, 88%): mp 132–134° C.; IR $\nu_{max}$ Nujol)/cm⁻¹ 3238, 2955, 2924, 1604, 1494, 1467, 1442, 1310, 1257, 1184, 1136, 1109 and 1079; NMR $\delta_H$ (400 MHz, CDCl₃) 3.08 (1H, d, J 5.0 Hz), 3.97 (3H, s), 6.82–6.87 (3H, m), 7.00 (1H, d, J 5.0 Hz), 7.29–7.34 (1H, m), 7.59 (1H, t, J 8.0 Hz), 8.09 (1H, d, J 6.0 Hz), 8.15 (1H, d, J 9.0 Hz) and 8.17 (1H,s).

Example 24

α-Phenyl-2-trifluoromethyl-4-quinolinemethanol

Isolated as a white crystalline solid, (270 mg, 77%): mp 141–142° C.; IR $\nu_{max}$ (Nujol)/cm⁻¹ 3252, 2925, 2849, 1595, 1513, 1465, 1363, 1303, 1296, 1255, 1213, 1181, 1166, 1154, 1132, 1100 and 1077; NMR $\delta_H$ (400 MHz, CDCl₃) 2.57 (1H, d, J 4 Hz), 6.54 (1H, d, J 3 Hz), 7.29–7.36 (5H, m), 7.54–7.57 (1H, m), 7.72–7.76 (1H, m), 7.92 (1H, d, J 8.5 Hz), 8.17 (1H, s) and 8.23 (1H, d, J 8.5 Hz); Anal. Calcd for $C_{17}H_{12}F_3NO \cdot 0.1 H_2O$: C, 66.93; H, 4.03; N, 4.59. Found: C, 66.79; H, 4.15; N, 4.58.

Example 25

8-Methoxy-α-phenyl-2-trifluoromethyl-4-quinolinemethanol

Isolated as a pale solid, (490 mg, 92%): m.p. 152–153° C.; IR $\nu_{max}$ (Nujol)/cm⁻¹ 3457, 2925, 2854, 1616, 1569, 1517, 1477, 1463, 1442, 1378, 1359, 1294, 1274, 1172, 1159, 1134, 1101 and 1020; NMR $\delta_H$ (400 MHz, CDCl₃) 2.51 (1H, d, J 2 Hz), 4.07 (3H, s), 6.49 (1H, d, J 3.5 Hz), 7.06 (1H, d, J 7.5 Hz), 7.31–7.35 (5H, m), 7.42–7.49 (2H, m) and 8.21 (1H, s); Anal. Calcd for $C_{18}H_{14}F_3NO$: C, 64.86; H, 4.23; N, 4.20. Found: C, 64.64; H, 4.25; N, 4.05.

Example 26

8-Methyl-α-phenyl-2-trifluoromethyl-4-quinolinemethanol

Isolated as a white solid, (240 mg, 44%): IR $\nu_{max}$ (Nujol)/cm⁻¹ 3190, 2925, 1457, 1268, 1145, 767 and 702; NMR $\delta_H$ (400 MHz, CDCl$_3$) 2.38 (1H, br s), 2.82 (3H, s), 6.52 (1H, s), 7.29–7.33 (5H, m), 7.41 (1H, t, J 8.5 Hz), 7.57 (1H, d, J 7.0 Hz), 7.73 (1H, d, J 8.6 Hz), and 8.13 (1H, s).

Example 27

α-(2-Chlorophenyl)-8-methyl-2-trinfluoromethyl-4-quinolinemethanol

Isolated as a yellow solid, (340 mg, 56%): m.p. 127–128° C.; IR ν$_{max}$ (Nujol)/cm$^{-1}$ 3251, 2924, 1469, 1268, 1121, 1038 and 762; NMR δ$_H$ (400 MHz, CDCl$_3$) 2.62 (1H, d, J 4.0 Hz), 2.84 (3H, s), 6.96–7.00 (2H, m), 7.14 (1H, t, J 7.6 Hz), 7.25–7.29 (1H, m), 7.43–7.49 (2H, m), 7.59–7.63 (2H, m), and 8.08 (1H, s); Anal. Calcd for C$_{18}$H$_{13}$ClF$_3$NO: C, 61.46; H, 3.72; N, 3.98. Found: C, 61.45; H, 3.76; N, 3.93.

Example 28

8-Methyl-α-(3-thienyl)-2-trifluoromethyl-4-quinolinemethanol

Isolated as a pale yellow solid, (159 mg, 29%): m.p. 113–114° C.; IR ν$_{max}$ (Nujol)/cm$^{-1}$ 3466, 2956, 1471, 1192, 1111 and 768; NMR δ$_H$ (400 MHz, CDCl$_3$) 2.83 (3H, s), 6.60 (1H, s), 6.99–7.00 (1H, m), 7.13 (1H, d, J 3.1 Hz), 7.26–7.28 (1H, m), 7.44 (1H, t, J 8.6 Hz), 7.59 (1H, d, J 7.0 Hz), 7.76 (1H, d, J 8.0 Hz) and 8.08 (1H, s); Anal. Calcd for C$_{16}$H$_{12}$F$_3$NOS.0.3 H$_2$O: C, 58.46; H, 3.86; N, 4.26. Found: C, 58.36; H, 3.79; N, 4.05.

Example 29

α-Cyclohexyl-8-methyl-2-trifluoromethy-4-quinolinemethanol

Isolated as a colourless gum, (231 mg, 41%): IR ν$_{max}$ (Nujol)/cm$^{-1}$ 3423, 2931, 1451, 1265, 1138 and 765; NMR δ$_H$ (400 MHz, CDCl$_3$) 1.07–1.34 (5H, m), 1.52–1.82 (6H, m), 2.08 (1H, d, J 3.1 Hz), 2.84 (3H, s), 5.30–5.31 (1H, m), 7.54 (1H, t, J 8.0 Hz), 7.64 (1H, d, J 7.0 Hz), and 7.86–7.90 (2H, m).

Example 30

8-Fluoro-α-phenyl-2-trifluoromethyl-4-quinolinemethanol

Isolated as an off-white solid, (224 mg, 41%): mp 102–103° C. (dec); IR ν$_{max}$ (Nujol)/cm$^{-1}$ 3406, 2924, 2854, 1475, 1294, 1143 and 754; NMR δ$_H$ (400 MHz, CDCl$_3$) 2.50 (1H, br s), 6.48 (1H, s), 7.32–7.51 (7H, m), 7.67 (1H, d, J 8.6 Hz) and 8.23 (1H, s); Anal. Calcd for C$_{17}$H$_{11}$F$_4$NO: C, 63.56; H, 3.45; N, 4.36. Found: C, 63.46; H, 3.48; N, 4.10.

Example 31

8-Ethyl-α-phenyl-2-trifluoromethy-4-quinolinemethanol

Isolated as an white solid, (411 mg, 75%): mp 102–104° C. ; IR ν$_{max}$ (Nujol)/cm$^{-1}$ 3275, 2924, 1450, 1269, 1186, 1143, 762 and 703; NMR δ$_H$ (400 MHz, CDCl$_3$) 1.35 (3H, t, J 7.6 Hz), 2.42 (1H, br s), 3.31 (2H, q, J 7.6 Hz), 6.51 (1H, s), 7.29–7.34 (5H, m), 7.45 (1H, t, J 15.6 Hz), 7.57 (1H, d, J 6.0 Hz), 7.73 (1H, d, J 8.6 Hz) and 8.12 (1H, s); Anal. Calcd for C$_{19}$H$_{16}$F$_3$NO: C, 68.88; H, 4.87; N, 4.23. Found: C, 68.88; H, 4.98; N, 4.13.

Example 32

8-Ethyl-α-(3-thienyl)-2-trifluoromethyl-4-quinolinemethanol

Isolated as a pale yellow waxy solid, (428 mg, 77%): IR ν$_{max}$ (Nujol)/cm$^{-1}$ 3318, 2967, 1269, 1138 and 765; NMR δ$^H$ (400 MHz, CDCl$_3$) 1.36 (3H, t, J 7.5 Hz), 2.49 (1H, br s), 3.33 (2H, q, J 7.5 Hz), 6.59 (1H, s), 7.01 (1H, d, J 5.0 Hz), 7.14 (1H, d, J 2.6 Hz), 7.27–7.29 (1H, m), 7.48 (1H, t J 8.4 Hz), 7.60 (1H, d, J 6.9 Hz), 7.77 (1H, d, J 8.5 Hz) and 8.07 (1H, s); Anal. Calcd for C$_{17}$H$_{14}$F$_3$NOS: C, 60.53; H, 4.18; N, 4.15. Found: C, 60.53; H, 4.42; N, 3.94.

Example 33

α-(4-Benzyloxyphenyl)-2,8-bis(trifluoromethyl)-4-quinolinemethanol

Isolated as a white solid, (156 mg, 37%): NMR δ$_H$ (400 MHz, CDCl$_3$) 5.04 (2H, s), 6.49 (1H, m), 6.94 (1H, d, J 25.0 Hz), 7.20–7.40 (8H, m), 7.55 (2H, m), 8.10 (2H, m) and 8.28 (1H, s).

Example 34

α-(3-Benzyloxyphenyl)-2,8-bis(trifluoromethyl)-4-quinolinemethanol

Isolated as a white solid, (140 mg, 25%): IR ν$_{max}$ (Nujol)/cm$^{-1}$ 3299, 2924, 1601, 1589, 1454, 1306, 1136, 768 and 693; NMR δ$_H$ (400 MHz, CDCl$_3$) 5.08 (2H, s), 6.42 (1H, m), 6.86 (1H,m), 6.95 (2H, m), 7.10–7.40 (6H, m), 7.58 (1H, t, J 8.0 Hz), 8.09 (2H, m) and 8.72 (1H, s).

Example 35

2-Dimethylamino-α-phenyl-4-quinolinemethanol

Isolated as a cream solid, (72 mg, 68%): mp 153.6–154.3° C.; IR ν$_{max}$ (Nujol)/cm$^{-1}$ 3400–3200, 3058, 2925, 2855, 1620, 1552, 1522, 1452, 1402, 1062 and 757; NMR δ$_H$ (400 MHz, CDCl$_3$) 3.22 (6H, s), 6.33 (1H, s), 7.04 (1H, t, J 7.5 Hz), 7.16 (1H, s), 7.28–7.33 (3H, m), 7.35–7.39 (2H, m), 7.44 (1H, t, J 7.1 Hz), 7.57 (1H, d, J 8.8 Hz) and 7.70 (1H, d, J 8.0 Hz).

Example 36

2-Methoxy-α-phenyl-4-quinolinemethanol

Isolated as a gummy solid, (129 mg, 49%): IR ν$_{max}$ (Nujol)/cm$^{-1}$ 3500–3200, 3065, 3030, 2948, 2896, 1614, 1574, 1474, 1437, 1387 and 1338; NMR δ$_H$ (400 MHz, CDCl$_3$) 2.37 (1H, d, J 3.9 Hz), 4.07 (3H, s), 6.37 (1H, d, J 3.3 Hz), 7.20–7.39 (7H, m), 7.54 (1H, t, J 7.0 Hz), 7.74 (1H, d, J 7.9 Hz) and 7.84 (1H, d, J 8.7 Hz).

Example 37

-α-Phenyl-8-trifluoromethy-4-quinolinemethanol

Isolated as a yellow gummy solid, (241 mg, 44%): IR ν$_{max}$ (Nujol)/cm$^{-1}$ 3374, 1598, 1310, 1134, 836 and 701; NMR δH (400 MHz, CDCl$_3$) 2.46 (1H, br s), 6.48 (1H, s), 7.30–7.36 (5H,m), 7.48 (1H, t, J 7.9 Hz), 7.81 (1H, d, J 4.6 Hz), 8.01 (1H, d, J 7.0 Hz), 8.11 (1H, d, J 8.5 Hz) and 9.11 (1H, d, J 4.5 Hz).

Example 38

α-(3-Thienyl)-8-trifluoromethy-4-quinolinemethanol

Isolated as a pale yellow glass, (280 mg, 50%): mp 114–116° C.; NMR δ$_H$ (400 MHz, CDCl$_3$) 2.44 (1H, br s), 6.56 (1H, s), 7.00 (1H, d, J 5.0 Hz), 7.16 (1H, d, J 3.0 Hz), 7.29–7.31 (1H, m), 7.51 (1H, t, J 7.5 Hz), 7.79 (1H, d, J 4.5 Hz), 8.03 (1H, d, J 7.1 Hz), 8.15 (1H, d, J 8.6 Hz) and 9.11

(1H, d, J 4.5 Hz); Anal. Calcd for $C_{15}H_{10}F_3NOS$: C, 58.25; H, 3.26; N, 4.53. Found: C, 57.93; H, 3.32; N. 4.29.

Example 39

2-Methyl-α-phenyl-4-quinolinemethanol

Isolated as a white solid, (186 mg, 37%): mp 192° C. (dec); IR $v_{max}$ (Nujol)/cm$^{-1}$ 3475, 3229, 2923, 2854, 2607, 1644, 1599, 1456, 1378 and 744; NMR $\delta_H$ (400 MHz, DMSOd$_6$) 3.05 (3H, s), 6.62 (1H, s), 7.22–7.28 (1H, m), 7.28–7.33 (2H, m), 7.47 (1H, d, J 7.1 Hz), 7.77 (1H, t, J 7.8 Hz), 8.0 (1H, t, J 7.3 Hz), 8.24 (1H, s) and 8.36–8.41 (2H, m); Anal. Calcd for $C_{17}H_{15}NO.HCl.0.25\ H_2O$: C, 70.34; H, 5.69; N, 4.82. Found: C, 70.35; H, 5.62; N, 4.84.

Example 40

2-Dibenzylamino-α-pheny-4-quinolinemethanol

Isolated as a pale yellow solid, (86 mg, 28%): mp 174.7–175.8° C.; IR $v_{max}$ (Nujol)/cm$^{-1}$ 3282, 3061, 2920, 2854, 1739, 1643, 1457, 1377 and 701; NMR $\delta_H$ (400 MHz, DMSO-d$_6$) 5.06–5.32 (4H, m), 6.26 (1H, s), 7.18–7.27 (4H, m), 7.27–7.45 (9H, m), 7.52–7.71 (2H, m) and 7.98–8.18 (2H, m).

Example 41

2-Phenyl-α-(3-thienyl)-4-quinolinemethanol

Isolated as an off-white solid, (250 mg, 46%): mp 158–159° C.; IR $v_{max}$ (Nujol)/cm$^{-1}$ 3302, 2925, 1595, 1461 and 767; NMR $\delta_H$ (400 MHz, DMSO-d$_6$) 6.32 (1H, d, J 4.5 Hz), 6.54 (1H, d, J 4.4 Hz), 7.07 (1H, d, J 5.0 Hz), 7.40–7.70 (5H, m), 7.72–7.74 (1H, m), 8.07 (1H, d, J 7.6 Hz), 8.20–8.27 (3H, m) and 8.34 (1H, s); Anal. Calcd for $C_{20}H_{15}NOS$: C, 75.68; H, 4.76; N, 4.41. Found: C, 75.01; H, 4.68; N, 4.22.

Example 42

2-Methyl-α-(3-thienyl)-4-quinolinemethanol

Isolated as a white solid, (275 mg, 54%): mp 200° C. (dec); IR $v_{max}$ (Nujol)/cm$^{-1}$ 3266, 3079, 2925, 2854, 2627, 1915, 1647, 1604, 1464, 1409, 1378 and 1086; NMR $\delta_H$ (400 MHz, DMSO-d$_6$) 3.02 (3H, s), 6.70 (1H, s), 7.09 (1H, d, J 5.0 Hz), 7.45–7.47 (1H, m), 7.51–7.54 (1H, m), 7.79 (1H, t, J 7.3 Hz), 8.02 (1H, t, J 7.2 Hz), 8.39 (1H, d, J 8.5 Hz) and 8.42 (1H, d, J 8.1 Hz) ; Anal. Calcd for $C_{15}H_{13}NOS.HCl$: C, 61.74; H, 4.84; N, 4.80. Found: C, 61.60; H, 4.81; N, 4.69.

Example 43

α-(3-Thienyl)-2-trifluoromethyl-4-quinolinemethanol

Isolated as a white solid, (270 mg, 71%): m.p. 144–146° C.; IR $v_{max}$ (Nujol)/cm$^{-1}$ 3829, 2925, 1596, 1466, 1376, 1365, 1310, 1254, 1212, 1182, 1164, 1130, 1101 and 1068; NMR $\delta_H$ (400 MHz, DMSO-d$_6$) 6.49 (1H, d, J 4.5 Hz), 6.54 (1H, d, J 4.5 Hz), 7.04 (1H, dd, J 2, 5 Hz), 7.54–7.55 (2H, m), 7.72–7.75 (1H, m), 7.87–7.91 (1H, m), 8.20 (1H, s), 8.17 (1H, d, J 7.5 Hz) and 8.33 (1H, d, J 8.5 Hz) .

Example 44

3-(2-trifluoromethyl-4-quinolinyl) tetrahydrothiophene-3-ol

Isolated as a white solid, (292 mg, 54%): m.p. 130–131° C.; IR $v_{max}$ (Nujol)/cm$^{-1}$ 3307, 2925, 1464, 1256, 1188 and 774; NMR $\delta_H$ (400 MHz, CDCl$_3$) 2.54–2.59 (1H, m), 2.67–2.80 (2H, m), 3.12–3.16 (1H, m), 3.23–3.34 (2H, m), 3.55 (1H, d, J 12.0 Hz), 7.68 (1H, t, J 7.0 Hz), 7.80 (1H, t, J 7.0 Hz), 7.96 (1H, s), 8.26 (1H, d, J 8.6 Hz) and 8.54 (1H, d, J 8.0 Hz) ; Anal. Calcd for $C_{14}H_{12}F_3NOS$: C, 56.18; H, 4.04; N, 4.68. Found: C, 56.24; H, 4.22; N, 4.63.

Example 45

4-(2,8-Bis(trifluoromethyl)-4-quinolinyl) tetrahydropyran-4-ol

Isolated as a white solid, (301 mg, 56%): m.p. 158–159° C.; IR $v_{max}$ (Nujol)/cm$^{-1}$ 3368, 2923, 1467, 1179, 1129 and 782; NMR $\delta_H$ (400 MHz, CDCl$_3$) 2.04–2.07 (3H, m), 2.47–2.54 (2H, m), 3.95–4.00 (2H, m), 4.07–4.14 (2H, m), 7.66–7.70 (1H, m), 7.79–7.83 (2H, m), 8.27 (1H, d, J 8.6 Hz) and 8.86 (1H, d, J 8.0 Hz); Anal. Calcd for $C_{15}H_{14}F_3NO_2$: C, 60.61; H, 4.75; N, 4.71. Found: C, 60.45; H, 4.81; N, 4.45.

Example 46

8-Methoxy-α-(3-thienyl)-2-trifluoromethyl-4-quinolinemethanol

Isolated as a white solid, (520 mg, 96%): m.p. 157–158° C.; IR $v_{max}$ (Nujol)/cm$^{-1}$ 3423, 2925, 2854, 1615, 1570, 1515, 1477, 1465, 1442, 1420, 1377, 1310, 1267, 1202, 1184, 1137, 1111, 1080 and 1018; NMR $\delta_H$ (400 MHz, CDCl$_3$) 2.49 (1H, d, J 4 Hz), 4.09 (3H, s), 6.59 (1H, d, J 4 Hz), 7.01–7.02 (1H, m), 7.09 (1H, dd, J 2, 7 Hz), 7.15–7.16 (1H, m), 7.30 (1H, dd, J 3, 5 Hz), 7.49–7.52 (2H, m) and 8.16 (1H, s).

Example 47

8-Chloro-α-(3-thienyl)-2-trifluoromethyl-4-quinolinemethanol

Isolated as a yellow solid, (137 mg, 25%): mp 132–133° C. IR $v_{max}$ (Nujol)/cm$^{-1}$ 3398, 1458, 1268, 1187 and 738; NMR $\delta_H$ (400 MHz, CDCl$_3$) 2.69 (1H, s), 6.43–6.46 (2H, m), 7.36 (1H, s), 7.55 (1H, t, J 8.7 Hz), 8.10 (1H, d, J 7.0 Hz) and 8.16–8.18 (2H, m); Anal. Calcd for $C_{15}H_{19}ClF_3NOS$: C, 52.41; H, 2.64; N, 4.07. Found: C, 52.49; H, 2.79; N, 3.77.

Example 48

2-Methoxy-α-(3-thienyl)-4-quinolinemethanol

Isolated as a pale yellow oil, (67 mg, 26%): NMR $\delta_H$ (400 MHz, CDCl$_3$ 2.43 (1H, d, J 4.0 Hz), 4.08 (3H, s), 6.45 (1H, d, J 2.9 Hz), 7.04 (1H, d, J 5.0 Hz), 7.18–7.19 (2H, m), 7.25–7.31 (2H, m), 7.57 (1H, t, J 7.0 Hz), 7.77 (1H, d, J 8.5 Hz) and 7.87 (1H, d, J 8.6 Hz).

Example 49

α-(2-Thienyl)-4-quinolinemethanol

Isolated as a cream solid, (224 mg, 54%): mp 173° C. (dec); IR $v_{max}$ (Nujol)/cm$^{-1}$ 3290, 3083, 3017, 2924, 2855, 2613, 1630, 1597, 1461, 1378, 1074 and 774; NMR $\delta_H$ (400 MHz, DMSO-d$_6$) 6.75 (1H, s), 7.07 (1H, d, J 5.0 Hz), 7.46–7.50 (2H, m), 7.85 (1H, t, J 7.8 Hz), 8.07 (1H, t, J 7.2 Hz), 8.28 (1H, d, J 5.6 Hz), 8.39 (1H, d, J 8.5 Hz), 8.50 (1H, d, J 8.0 Hz), and 9.31 (1H, d, J 5.5 Hz); Anal. Calcd for $C_{14}H_{11}NOS.HCl.0.2\ H_2O$: C, 59.76; H, 4.44; N, 4.98. Found: C, 59.84; H, 4.21; N, 4.93.

Example 50

2,8-Bis(trifluoromethyl)-α-(2-furyl)-4-quinolineethanol

Isolated as an off-white solid, (160 mg, 29%): IR $v_{max}$ (Nujol)/cm$^{-1}$ 3557, 3364, 2921, 1586, 1114 and 735; NMR $\delta_H$ (400 MHz, CDCl$_3$) 2.10 (3H, s), 2.66 (1H, s), 6.41–6.43 (2H, m), 7.33 (1H, s), 7.52 (1H, t, J 8.7 Hz), 8.07 (1H, d, J 7.0 Hz) and 8.16 (2H, m).

Example 51

α-(2-Benzofuranyl)-2,8-bis(trifluoromethyl)-4-quinolineethanol

Isolated as a white solid, (121 mg, 20%): mp 123–124° C.; IR $v_{max}$ (Nujol)/cm$^{-1}$ 3509, 2925, 1456, 1309, 1154, 1109 and 742; NMR $\delta_H$ (400 MHz, CDCl$_3$) 2.22 (3H, s), 2.84 (1H, s), 6.79 (1H, s), 7.23–7.30 (3H, m), 7.35 (1H, d, J 8.0 Hz), 7.49 (1H, t, J 8.6 Hz), 7.57 (1H, d, J 7.0 Hz), 8.06 (1H, d, J 7.2 Hz), 8.23 (1H, s) and 8.32 (1H, d, J 8.1 Hz); Anal. Calcd for C$_{21}$H$_{13}$F$_6$NO$_2$: C, 56.89; H, 3.41; N, 3.16. Found: C, 56.96; H, 3.07; N, 2.90.

Example 52

8-(2,8-Bis(trifluoromethyl)-4-quinoliny)-1,4-dioxaspiro[4.5]decan-8-ol

Isolated as a pale brown crystalline solid, (684 mg, 56%): mp 146–147° C.; IR $v_{max}$ (Nujol)/cm$^{-1}$ 3509, 2925, 1316, 1210, 1117 and 773; NMR $\delta_H$ (400 MHz, CDCl$_3$) 1.77–1.82 (1H, m), 1.97–2.00 (1H, m), 2.08–2.17 (1H, m), 2.19–2.25 (1H, m), 2.47 2.54 (3H, m), 4.01–4.05 (5H, m), 7.70 (1H, t, J 8.5 Hz), 7.97 (1H, s), 8.12 (1H, d, J 6.9 Hz), and 9.06 (1H, d, J 8.6 Hz); Anal. Calcd for C$_{19}$H$_{17}$F$_6$NO$_3$: C, 54.16; H, 4.07; N, 3.32. Found: C, 54.29; H, 4.13; N, 3.10.

Example 53

1-(2,8-Bis(trifluoromethyl)-4-quinolinyl)cyclopent-2-ene-1-ol

Isolated as a white solid, (370 mg, 73%): mp 73–74° C.; IR $v_{max}$ (Nujol)/cm$^{-1}$ 3354, 2925, 1459, 1310, 1139 and 773; NMR $\delta_H$ (400 MHz, CDCl$_3$) 2.40–2.47 (1H, m), 2.53–2.62 (2H, m), 2.75–2.83 (1H, m), 6.12–6.14 (1H, m), 6.34–6.36 (1H, m), 7.67 (1H, t, J 7.6 Hz), 7.86 (1H, s), 8.13 (1H, d, J 6.5 Hz), and 8.77 (1H, d, J 7.9 Hz).

Example 54

α-Cyclohexyl-2,8-dimethyl-4-quinolinemethanol

Isolated as a white solid, (4.5 g, 76%): m.p. 155–157° C.; IR $v_{max}$ (Nujol)/cm$^{-1}$ 3348, 2924, 2853, 1601, 1568, 1505, 1464, 1377, 1336 and 1039; NMR $\delta_H$ (400 MHz, CDCl$_3$) 1.11–1.22 (5H, m), 1.46–1.48 (1H, m), 1.69–1.80 (5H, m), 2.16 (1H, d, J 3.5 Hz), 2.80 (3H, s), 5.13 (1H, t, J 3.5 Hz), 7.31–7.35 (2H, m), 7.50 (1H, d, J 3.0 Hz) and 7.75 (1H, d, J 4.5 Hz); Anal. Calcd for C$_{18}$H$_{23}$NO: C, 80.26; H, 8.61; N, 5.20. Found: C, 80.30; H, 8.76; N, 5.14.

Example 55

2-Bromo-α-cyclohexyl-8-methyl-4-quinolinemethanol

Isolated as a cream solid, (1.2 g, 75%): IR $v_{max}$ (Nujol)/cm$^{-1}$ 3471, 3071, 2925, 2854, 1562, 1460, 1377, 1281, 1108, 874 and 764; NMR $\delta_H$ (400 MHz, CDCl$_3$) 1.07–1.33 (5H, m), 1.50–1.55 (1H, m), 1.62–1.80 (5H, m), 1.88–2.14 (1H, s), 2.76 (3H, s), 5.18 (1H, d, J 5.1 Hz), 7.43 (1H, t, J 7.8 Hz), 7.55 (1H, d, J 7.1 Hz), 7.62 (1H, s) and 7.78 (1H, s).

Example 56

4-(1-Cyclohexyl-1-hydroxymethyl)-8-methyl-2-quinolinecarboxaldehyde

Isolated as a cream foam, (52 mg, 48%): IR $v_{max}$ (Nujol)/cm$^{-1}$ 3600–3400, 2924, 2854, 1711, 1590, 1459, 1377 and 764; NMR $\delta_H$ (400 MHz, CDCl$_3$) 1.09–1.31 (5H, m), 1.46–1.51 (1H, m), 1.53–1.56 (1H, m), 1.63–1.64 (1H, m), 1.69–1.76 (2H, m), 1.81–1.88 (1H, m), 2.10 (1H, d, J 3.6 Hz), 5.26 (1H, dd, J 5.4, 3.1 Hz), 7.69 (1H, t, J 7.8 Hz), 7.81 (1H, t, J 7.0 Hz), 8.12–8.16 (2H, m), 8.28 (1H, d, J 8.5 Hz) and 10.22 (1H, s).

Example 57

α-Cyclohexyl-8-methyl-4-quinolinemethanol

Isolated as a pale solid, (5.1 g, 79%): m.p. 138–139° C.; IR $v_{max}$ (Nujol)/cm$^{-1}$ 3421, 2919, 2856, 1591, 1570, 1512, 1455, 1450, 1377, 1346, 1239, 1156, 1100 and 1084; NMR $\delta_H$ (400 MHz, CDCl$_3$) 1.11–1.29 (5H, m), 1.49–1.52 (1H, m), 1.63–1.82 (5H, m), 2.19 (1H, d, J 3.5 Hz), 2.82 (3H, s), 5.24 (1H, m), 7.43 (1H, t, J 7.5 Hz), 7.50 (1H, d, J 4.5 Hz), 7.56 (1H, d, J 7.0 Hz), 7.87 (1H, d, J 8.0 Hz) and 8.90 (1H, d, J 4.5 Hz); Anal. Calcd for C$_{17}$H$_{21}$NO: C, 79.96; H, 8.29; N, 5.48. Found: C, 79.80; H, 8.39; N, 5.37.

Example 58

2-Bromo-α-cyclohexyl-4-quinolinemethanol

Isolated as an off-white solid, (1.63 g, 53%): mp 114.5–115.6° C.; IR $v_{max}$ (Nujol)/cm$^{-1}$ 3400–3300, 2925, 2855, 1577, 1557, 1455, 1377, 1278, 1101 and 766; NMR $\delta_H$ (400 MHz, CDCl$_3$) 2.24 (1H, d, J3.5 Hz), 5.19 (1H, t, J 4.2 Hz), 7.54–7.58 (1H, m), 7.64 (1H, s), 7.69–7.73 (1H, m), 7.97 (1H, d, J 7.5 Hz) and 8.05 (1H, d, J 8.7 Hz).

Example 59

α-Cyclohexyl-2-methoxy-4-quinolinemethanol hydrochloride

Isolated as a white solid, (143 mg, 61%): mp 155.9–156.3° C.; IR $v_{max}$ (Nujol)/cm$^{-1}$ 3255, 2923, 2854, 2489, 1871, 1644, 1606, 1461, 1359, 1062, 869 and 755; NMR $\delta_H$ (400 MHz, CDCl$_3$) 1.01–1.31 (5H, m), 1.46–1.49 (1H, m), 1.57–1.67 (5H, m), 4.02 (3H, s), 5.04 (1H, d, J 5.0 Hz), 7.05 (1H, s), 7.46 (1H, t, J 7.1 Hz), 7.68 (1H, t, J 7.5 Hz), 7.84 (1H, d, J 8.1 Hz) and 8.09 (1H, d, J 8.7 Hz); Anal. Calcd for C$_{17}$H$_{21}$NO$_2$·HCl: C, 66.33; H, 7.20; N, 4.55. Found: C, 66.09; H, 7.14; N, 4.48.

Example 60

2-Amino-α-cyclohexyl-4-quinolinemethanol

Isolated as a white solid, (40 mg, 16%): IR $v_{max}$ (Nujol)/cm$^{-1}$ 3461, 3404, 3322, 3147, 3064, 2927, 2854, 1658, 1617, 1566, 1455, 1431, 1378, 1098 and 752; NMR $\delta_H$ (400 MHz, CDCl$_3$) 1.02–1.32 (5H, m), 1.51–1.69 (6H, m), 4.92 (1H, t, J 4.3 Hz), 5.30 (1H, d, J 4.0 Hz), 6.38 (2H, s), 6.86 (1H, s), 7.15 (1H, t, J 7.3 Hz), 7.42–7.48 (2H, m), and 7.81 (1H, d, J 8.5 Hz).

Example 61

N-Benzyl-4-(1-cyclohexyl-1-hydroxymethyl)-2-quinolinecarboxamide

Isolated as a white solid, (41 mg, 15%): mp 152.8–153.3° C.; IR $\nu_{max}$ (Nujol)/cm$^{-1}$ 3382, 3500–3300, 2925, 2853, 1665, 1533, 1506, 1452 and 768; NMR $\delta_H$ (400 MHz, CDCl$_3$) 1.12–1.26 (5H, m), 1.41–1.45 (1H, m), 1.59–1.77 (3H, m), 1.85–1.90 (2H, m), 2.25 (1H, d, J 4.0 Hz), 4.74 (2H, d, J 6.0 Hz), 5.24 (1H, t, J 4.8 Hz), 7.29–7.43 (5H, m), 7.62 (1H, t, J 7.0 Hz), 7.74 (1H, t, J 7.8 Hz), 8.09 (1H, d, J 8.5 Hz), 8.16 (1H, d, J 7.6 Hz), 8.42 (1H, s) and 8.60 (1H, t, J 5.7 Hz); Anal. Calcd for C$_{24}$H$_{26}$N$_2$O$_2$: C, 76.98; H, 7.00; N, 7.48. Found: C, 76.74; H, 6.93; N, 7.42.

Example 62

2-Methoxy-α-(2-pyridyl)-4-quinolinemethanol

Isolated as a white solid, (278 mg, 72%): IR $\nu_{max}$ (Nujol)/cm$^{-1}$ 3064, 2929, 2854, 1617, 1575, 1388, 1343, 1236, 1047 and 749; NMR $\delta_H$ (400 MHz, CDCl$_3$) 4.06 (3H, s), 6.32 (1H, s), 6.95 (1H, s), 7.10 (1H, d, J 11.0 Hz), 7.20 (1H, m), 7.32 (1H, t, J 6.5 ), 7.58 (2H, t, J 6.5 Hz), 7.86 (1H, d, J 8.0 Hz), 7.97 (1H, d, J 8.0 Hz) and 8.64 (1H, d, J 5.0 Hz).

Example 63

2-Amino-8-α-(2-pyridyl)-4-quinolinemethanol

Isolated as a cream solid, (376 mg, 26%): mp 159° C. (dec); IR $\nu_{max}$ (Nujol)/cm$^{-1}$ 3426, 3304, 3126, 2924, 2854, 1645, 1618, 1595, 1568, 1466, 1430, 1077 and 752; NMR $\delta_H$ (400 MHz, CDCl$_3$) 6.22 (1H, d, J 4.6 Hz), 6.33 (1H, d, J 4.6 Hz), 6.44 (2H, s), 7.03 (1H, s), 7.06 (1H, t, J 7.6 Hz), 7.26 (1H, t, J 6.8 Hz), 7.35–7.45 (2H, m), 7.54 (1H, d, J 8.0 Hz), 7.77–7.82 (1H, m), 7.91 (1H, d, J 7.5 Hz), 8.47 (1H, dd, J 5.0, 1.0 Hz); Anal. Calcd for C$_{15}$H$_{13}$N$_3$O.0.25 H$_2$O: C, 70.43; H, 5.32; N, 16.43. Found: C, 70.50; H, 5.29; N, 16.11.

Example 64

2-Bromo-8-methyl-α-(2-pyridyl)-4-quinolinemethanol

Isolated as a white solid, (170 mg, 31%): mp 149° C. (dec); NMR $\delta_H$ (400 MHz, CDCl$_3$) 2.74 (3H, s), 6.41 (1H, s), 7.31 (2H, m), 7.40 (1H, m), 7.54 (1H, d, J 7.0 Hz), 7.66 (1H, dt, J 11.0, 3.0 Hz), 7.80 (1H, s), 7.98 (1H, d, J 9.0 Hz) and 8.56 (1H, d, J 5.0 Hz).

Example 65

2-Bromo-8-methyl-α-phenyl-4-quinolinemethanol

Isolated as an orange foam, (72 mg, 23%): mp 130.7–131.8° C.; IR $\nu_{max}$ (Nujol)/cm$^{-1}$ 3500–3300, 3075, 2924, 2855, 1585, 1561, 1454, 1297, 1113, 1048, 754, 702 and 594; NMR $\delta_H$ (400 MHz, CDCl$_3$) 2.34 (1H, d, J 4.1 Hz), 2.75 (3H, s), 6.42 (1H, d, J 2.9 Hz), 7.30–7.37 (6H, m), 7.49 (1H, d, J 7.0 Hz), 7.64 (1H, d, J 8.6 Hz) and 7.89 (1H, s).

Example 66

8-Fluoro-α-(3-thienyl)-2-trifluoromethyl-4-quinolinemethanol

Isolated as a brown gum, (303 mg, 54%): IR $\nu_{max}$ (Nujol)/cm$^{-1}$ 3396, 3107, 1512, 1478, 1146 and 754; NMR $\delta_H$ (400 MHz, CDCl$_3$) 2.57 (1H, br s), 6.58 (1H, s), 6.99 (1H, d, J 5.0 Hz), 7.17 (1H, d, J 3.4 Hz), 7.29–7.31 (1H, m), 7.42–7.55 (2H, m), 7.72 (1H, d, J 8.5 Hz) and 8.18 (1H, s).

Example 67

2-Methoxy-8-methyl-α-(2-pyridyl)-4-quinolinemethanol

Isolated as a cream solid, (848 mg, 64%): mp 126.8–127.6° C.; IR $\nu_{max}$ (Nujol)/cm$^{-1}$ 3200–3000, 2924, 2854, 1615, 1598, 1585, 1478, 1343 and 754; NMR $\delta_H$ (400 MHz, CDCl$_3$) 2.69 (3H, s), 4.05 (3H, s), 5.16–5.43 (1H, s), 6.33 (1H, s), 6.96 (1H, s), 7.08 (1H, d, J 8.1 Hz), 7.18–7.27 (2H, m), 7.46 (1H, d, J 7.1 Hz), 7.53–7.57 (1H, m), 7.83 (1H, d, J 8.7 Hz) and 8.62 (1H, d, J 5.1 Hz); Anal. Calcd for C$_{17}$H$_{16}$N$_2$O$_2$.0.1 H$_2$O: C, 72.37; H, 5.79; N, 9.93. Found: C, 72.21; H, 5.71; N, 9.86.

Example 68

2-Methoxy-8-methyl-α-phenyl-4-quinolinemethanol

Isolated as a white solid, (97 mg, 37%): IR $\nu_{max}$ (Nujol)/cm$^{-1}$ 3548, 3300–3200, 3067, 3006, 2924, 2854, 1612, 1584, 1481, 1456, 1442, 1382, 1337, 1129 and 754; NMR $\delta_H$ (400 MHz, CDCl$_3$) 2.30 (1H, s), 2.71 (3H, s), 4.10 (3H, s), 6.39 (1H, s), 7.15–7.19 (1H, m), 7.23 (1H, s), 7.25–7.46 (6H, m) and 7.61 (1H, d, J 8.7 Hz); Anal. Calcd for C$_{18}$H$_{17}$NO$_2$.0.2 H$_2$O: C, 76.41; H, 6.20; N, 4.95. Found: C, 76.44; H, 6.02; N, 4.93.

The following novel synthetic intermediates were synthesised using Method A from the appropriately substituted 4-bromoquinoline and the appropriate carbonyl compound:

1-Benzyl-4-(2,8-bis(trinfluoromethyl)-4-quinolinyl)-4-piperidinol

Isolated as a clear, viscous syrup, (480 mg, 73%): NMR $\delta_H$ (400 MHz, CDCl$_3$) 2.01–2.14 (2H, m), 2.39–2.47 (2H, m), 2.61–2.76 (3H, m), 2.91 (2H, m), 3.62 (2H, d, J 5.6 Hz), 7.26–7.39 (5H, m), 7.69–7.73 (1H, m), 7.89 (1H, s), 8.14 (1H, d, J 7.2 Hz) and 9.16 (1H, d, J 8.8 Hz).

3-(2,8-Bis(trifluoromethyl)-4-quinolinyl)-1-dipbenylmethyl-3-azetidinol

Isolated as a pale yellow foam, (738 mg, 100%): IR $\nu_{max}$ (Nujol)/cm$^{-1}$ 3378, 2924, 1456, 1377, 1311, 1145 and 702; NMR $\delta_H$ (400 MHz, CDCl$_3$) 3.74–3.79 (4H, m), 4.45 (1H, s), 7.21–7.37 (6H, m), 7.41–7.46 (4H, m), 7.65–7.69 (2H, m), 8.15 (1H, d, J 7.1 Hz) and 8.35 (1H, d, J 8.6 Hz).

1-(2,8-Bis(trifluoromethyl)-4-quinolinyl)-4-bydroxybutanone

Isolated as a yellow oil, (1.54 g, 88%): IR $\nu_{max}$ (Nujol)/cm$^{-1}$ 3600–3100, 2962, 2894, 1705, 1426, 1310, 1274, 1190, 1143 and 1109; NMR $\delta_H$ (400 MHz, CDCl$_3$) (tautomer 1) 2.30–2.44 (1H, m), 2.66–2.73 (1H, m), 2.94 (1H, s), 4.08–4.13 (1H, m), 4.21–4.30 (1H, m), 4.31–4.36 (1H, m), 7.72 (1H, t, J 8.1 Hz), 8.14–8.17 (2H, m) and 8.75 (1H, d, J 8.5 Hz); (tautomer 2) 2.03–2.14 (4H, m), 3.80 (2H, t, J 5.9 Hz), 7.79 (1H, t, J 8 Hz), 8.00 (1H, s), 8.22 (1H, d, J 7.0 Hz) and 8.55 (1H, d, J 9.3 Hz).

1-(2,8-Bis(trifluoromethyl)-4-quinolinyl)-5-hydroxypentanone

Isolated as a white solid, (1.28 g, 70%): m.p. 120.8–121.3° C.; TR $\nu_{max}$ (Nujol)/cm$^{-1}$ 3394, 3128, 3088, 2956, 2924, 2854, 1463, 1424, 1377, 1313 and 1198; NMR $\delta_H$ (400 MHz, CDCl$_3$) (tautomer 1) 1.64–1.83 (4H, m), 2.03–2.12 (2H, m), 3.91 (1H, dd, J 11.0, 4.5 Hz), 4.18 (1H, dt, J 11.0, 2.2 Hz), 7.02–7.10 (1H, s), 7.95 (1H, t, J 8 Hz), 8.19 (1H, s), 8.37 (1H, d, J 7 Hz), and 9.18 (2H, d, J 7.8 Hz); (tautomer 2) 1.50–1.57 (2H, m), 1.64–1.83 (2H, m), 3.27 (2H, t, J 7.3 Hz), 3.46 (2H, t, J 6.2 Hz), 4.45–4.52 (1H, s), 8.01 (1H, t, J 8 Hz), 8.44 (1H, d, J 7.1 Hz), 8.49 (1H, d, J 8.5 Hz) and 8.53 (1H, s).

Isobutyl 4-(α-hydroxycyclohexylmethyl)-8-methylquinoline-2-carboxylate

Isolated as a white solid, (170 mg, 27%): NMR $\delta_H$ (400 MHz, CDCl$_3$) 0.90 (3H, d, J 6.4 Hz), 0.92 (3H, d, J 6.0 Hz), 1.12–1.19 (3H, m), 1.22–1.29 (2H, m), 1.33–1.37 (1H, m), 1.64–1.68 (2H, m), 1.76–1.77 (1H, m), 1.85–1.99 (3H, m), 2.84 (3H, s), 3.80–3.90 (1H, m), 6.11 (1H, d, J 7.0 Hz), 7.69 (1H, t, J 7.1 Hz), 7.63 (1H, d, J 7.0 Hz), 8.05 (1H, d, J 7.9 Hz), and 8.32 (1H, s).

2-Bromo-α-phenyl-4-quinolinemethanol

Isolated as a pale yellow oil, (307 mg, 51%): IR $\nu_{max}$ (Nujol)/cm$^{-1}$ 3500–3300, 3064, 3032, 2921, 1580, 1558, 1508, 1454, 757, 736 and 700; NMR $\delta_H$ (400 MHz, CDCl$_3$) 2.55 (1H, d, J 4.0 Hz), 6.43 (1H, d, J 3.3 Hz), 7.27–7.39 (5H, m), 7.44 (1H, t, J 7.8 Hz), 7.65 (1H, t, J 7.0 Hz), 7.82 (1H, d, J 8.7 Hz), 7.91 (1H, s) and 8.03 (1H, d, J 7.6 Hz).

Method B

Example 69

2,8-Bis(trifluoromethyl)-α-ethoxymethyl-4-quinolinemethanol

A solution of (2,8-bis(trifluoromethyl)-4-quinolinyl) oxirane (208 mg, 0.68 mmol) in ether (3 mL) was treated with BF$_3$.etherate (0.2 mL), stirred at room temperature for 2 h, poured into dilute NaHCO$_3$ (20 mL) and extracted with EtOAc (2×20 mL). The combined extracts were dried (MgSO$_4$), concentrated in vacuo and the residue purified by flash chromatography [SiO$_2$; heptane-EtOAc (2:1)] to give the title compound (196 mg, 82%) as a yellow oil: IR $\nu_{max}$ (Nujol)/cm$^{-1}$ 3700–3200, 3087, 2982, 2879, 1606, 1586, 1431, 1372, 1311, 1191, 1144, 1109, 769; NMR $\delta_H$ (400 MHz, CDCl$_3$) 1.26 (3H, t, J 7.0 Hz), 3.24–3.31 (1H, br s), 3.48 (1H, dd, J 8.4, 9.6 Hz), 3.54–3.69 (2H, m), 3.84 (1H, dd, J 9.6, 3.2 Hz), 5.70 (1H, dd, J 8.4, 3.2 Hz), 7.75 (1H, t, J 7.9 Hz), 8.13 (1H, s), 8.17 (1H, d, J 7.5 Hz), 8.28 (1H, d, J 9.1 Hz); M/Z 354 (M+H)$^+$.

Method C

Example 70

4-(2,8-Bis(trifluoromethyl)-4-quinolinyl)-4-piperidinol

A solution of 1-benzyl-4-(2,8-bis(trifluoromethyl)-4-quinolinyl)-4-piperidinol (480 mg, 1.06 mmol) and palladium hydroxide (100 mg) in MeOH (25 mL) was stirred vigorously under an atmosphere of hydrogen (using balloons) for 3 h, filtered through a pad of celite and concentrated in vacuo. The resulting viscous syrup was triturated with ether to give the title compound (241 mg, 63%) as a pale-grey solid: mp 210–220° C. (dec); IR $\nu_{max}$ (Nujol)/cm$^{-1}$ 3406, 2924, 1458, 1313, 1154 and 823; NMR $\delta_H$ (400 MHz, DMSO-d$_6$) 1.89 (2H, d, J 13.1 Hz), 2.11–2.19 (2H, m), 2.85 (2H, br d, J 10.0 Hz), 3.05–3.10 (2H, m), 5.73 (1H, s), 7.90 (1H, t, J 8.6 Hz), 8.03 (1H, s), 8.34 (1H, d, J 7.0 Hz) and 9.34 (1H, d, J 8.3 Hz).

Method D

Example 71

3-(2,8-Bis(trifluoromethyl)-4-quinolinyl)-3-azetidinol

To a stirred solution of 3-(2,8-bis(trifluoromethyl)-4-quinolinyl)-1-diphenylmethyl-3-azetidinol (690 mg, 1.37 mmol) in dichloroethane (20 mL), at 0° C., was added dropwise 1-chloroethyl chloroformate (0.18 mL, 1.2 eq). The mixture was stirred at 70° C. for 1 h and concentrated in vacuo. The residue was dissolved in MeOH (20 mL), stirred at room temperature for 17 h, concentrated in vacuo and the residue triturated with ether to give the title compound (351 mg, 69%) as a pale-yellow solid: mp 201° C. (dec); NMR $\delta_H$ (400 MHz, CDCl$_3$) 4.44–4.45 (2H, m), 4.76–4.78 (2H, m), 7.95–7.99 (1H, m), 8.23 (1H, s), 8.38–8.42 (2H, m), 9.00 (1H, br s), 9.47 (1H, br s); Anal. Calcd for C$_{14}$H$_{11}$ClF$_6$N$_2$O: C, 45.12; H, 2.97; N, 7.51. Found: C, 45.21; H, 3.29; N, 7.08.

Method E

Example 72

4-(α-Methoxybenzyl)-2,8-bis(trifluoromethyl) quinoline

A solution of α-phenyl-2,8-bis(trifluoromethyl)quinoline-4-methanol (50 mg, 0.13 mmol) in anhydrous THF (4 mL) was treated with NaH (18 mg, 60% dispersion in oil, 0.44 mmol), stirred at room temperature for 2 min, treated with iodomethane (0.8 mL, 1.2 mmol) and stirred for 15 min. The solution was then treated with water (10 mL), extracted with ether (2×10 mL), the extracts washed with water (10 mL), dried (MgSO$_4$), concentrated in vacuo and purified by chromatography [SiO$_2$; heptane-EtOAc (10:1)] to give the title compound (41 mg, 79%) as a pale solid: mp 115–117° C.; IR $\nu_{max}$ (liquid film)/cm$^{-1}$ 3070, 2929, 2854, 1589, 1588, 1517, 1491, 1456, 1429, 1378, 1210, 1276, 1211, 1184, 1164, 1129 and 1101; NMR $\delta_H$ (400 MHz, CDCl$_3$) 3.47 (3H, s), 5.90 (1H, s), 7.29–7.35 (5H, m), 7.60–7.64 (1H, t J 8 Hz) and 8.25 (1H, d J 8 Hz).

Method F

Example 73

2,8-Bis(trifluoromethyl)-α-(3-hydroxyphenyl)-4-quinolinemethanol

A solution of α-(3-benzyloxyphenyl)-2,8-bis (trifluoromethyl)-4-quinolinemethanol (80 mg, 0.17 mmol) in EtOH (4 mL) was treated with 10% Pd/C (5 mg), hydrogenated for 2 h, filtered to remove the catalyst, concentrated in vacuo and the resulting oil purified by chromatography [SiO$_2$; heptane-EtOAc (1:1)] to give the title compound (36 mg, 53%) as an oil: NMR $\delta_H$ (400 MHz, CDCl$_3$) 5.35 (1H, br s), 6.45 (1H, s), 6.65–6.80 (2H, m), 6.91 (1H, d, J 10.0 Hz), 7.21 (1H, t, J 7.0 Hz), 7.59 (1H, t, J 9.0 Hz), 8.12 (2H, t, J 9.0 Hz) and 8.22 (1H, s).

Example 74

2,8-Bis(trifluoromethyl)-α-(4-hydroxyphenyl)-4-quinolinemethanol

Isolated as a yellow solid, (112 mg, 25%): IR $\nu_{max}$ (Nujol)/cm$^{-1}$ 3385, 3201, 2924, 1611, 1515, 1461, 1310,

Method G

Example 75

2,8-Bis(trifluoromethyl)-α-(3-hydroxymethylphenyl)-4-quinolinemethanol 2,8-Bis(trifluoromethyl)-α-(3-tert-butyldimethylsilyloxymethylphenyl)-4-quinolinemethanol This was prepared from 2,8-bis(trifluoromethyl)-4-bromoquinoline by the method of Example 1 using 3-(tert-butyldimethylsilyloxymethyl)benzaldehyde in place of benzaldehyde and the crude product used directly in the next step.

2,8-Bis(trifluoromethyl)-α-(3-hydroxymethylphenyl)-4-quinolinemethanol

A solution of 2,8-bis(trifluoromethyl)-α-(3-tert-butyldimethylsilyloxymethylphenyl)-4-quinolinemethanol (crude, 1.17 mmol) in THF (5 mL) was treated with tetrabutylammonium fluoride (1-M in UHF, 0.7 mL, 0.7 mmol), stirred for 15 min, washed with water (2×2 mL), concentrated in vacuo and the resulting oil purified by chromatography [$SiO_2$; heptane-EtOAc (3:1–1:1)] to give the title compound (117 mg, 25%) as a white solid: mp 152–154° C.; IR $v_{max}$ (Nujol)/cm$^{-1}$ 3359, 3206, 2924, 1458, 1378, 1308, 1184, 1155, 1136, 1115, 1083, 1032, 766 and 695; NMR $\delta_H$ (400 MHz, CDCl$_3$) 3.05 (1H, br s), 6.63 (2H, s), 6.48 (1H, s), 7.10–7.40 (4H, m), 7.68 (1H, m), 8.05–8.15 (2H, m), and 8.21 (1H, s).

Method H

Example 76

α-(2-Aminophenyl)-2,8-bis(trifluoromethyl)-4-quinolinemethanol

A solution of 2,8-bis(trifluoromethyl)-α-(2-nitrophenyl)-4-quinolinemethanol (636 mg, 1.53 mmol) in EtOH (30 mL) was treated with zinc dust (994 mg, 15.3 mmol) and CaCl$_2$ (170 mg, 1.53 mmol), refluxed for 3 h, cooled, filtered through a pad of celite, concentrated in vacuo, purified by chromatography [$SiO_2$; $CH_2Cl_2$] and the resulting solid recrystallised from $CH_2Cl_2$/heptane to give the title compound (202 mg, 34%) as a cream solid: mp 145.9–146.2° C.; IR $v_{max}$ (Nujol)/cm$^{-1}$ 3413, 3339, 3094, 2924, 2854, 1611, 1586, 1462, 1313, 1295, 1155, 1132, 1111 and 1073; NMR $\delta_H$ (400 MHz, CDCl$_3$) 1.40–1.79 (1H, s), 2.39–3.14 (1H, s), 3.84–4.58 (2H, s), 6.48–6.50 (1H, m), 6.59–6.62 (2H, m), 6.83 (1H, d, J 6.5 Hz), 7.15–7.18 (1H, m), 7.59 (1H, t, J 8.1 Hz), 7.99 (1H, d, J 9.0 Hz), 8.12 (1H, d, J 6.9 Hz) and 8.18 (1H, s); Anal. Calcd for $C_{18}H_{12}F_6N_2O.0.25\ H_2O$: C, 55.32; H, 3.22; N, 7.17. Found: C, 55.33; H, 3.34; N, 7.03.

Method I

4-Bromo-N,N-dimethyl-2-quinolineamine

A solution of 2,4-dibromoquinoline (273 mg, 1.0 mmol) in EtOH (15 mL) was treated with aqueous dimethylamine (40%, 0.4 mL, 3 mmol), stirred at room temperature for 16 h, concentrated in vacuo and purified by chromatography [$SiO_2$; heptane-EtOAc (9:1)] to give the product (119 mg, 50%) as a cream solid: IR $v_{max}$ (Nujol)/cm$^{-1}$ 2924, 2854, 1598, 1546, 1510, 1463, 1379 and 754; NMR $\delta_H$ (400 MHz, CDCl$_3$) 3.21 (6H, s), 7.21 (1H, s), 7.23–7.26 (1H, m), 7.55 (1H, t, J 8.2 Hz), 7.68 (1H, d, J 8.5 Hz) and 7.94 (1H, d, J 7.1 Hz); M/Z 251 (M+H)$^+$.

The following compounds (Examples 77–80) were prepared using Method I from the appropriately substituted 2-bromoquinoline and the appropriate nucleophile:

Example 77

α-Cyclohexyl-2-methoxy-8-methyl-4-quinolinemethanol

Isolated as a cream solid, (133 mg, 82%): IR $v_{max}$ (Nujol)/cm$^{-1}$ 3500–3300, 2925, 2854, 1610, 1583, 1480, 1440, 1379, 1339, 1233, 1044 and 758; NMR $\delta_H$ (400 MHz, CDCl$_3$) 1.03–1.31 (5H, m), 1.52–1.82 (6H, m), 1.88–1.99 (1H, m), 2.71 (3H, s), 4.06 (3H, s), 5.11 (1H, d, J 5.6 Hz), 7.00 (1H, s), 7.24–7.28 (1H, m), 7.47 (1H, d, J 7.0 Hz) and 7.72 (1H, d, J 8.3 Hz); Anal. Calcd for $C_{18}H_{23}NO_2.0.1\ H_2O$: C, 75.28; H, 8.14; N, 488. Found: C, 75.14; H, 8.08; N, 4.80.

Example 78

α-Cyclohexyl-2-methylthio-4-quinolinemethanol

Isolated as a white foam, (101 mg, 70%): IR $v_{max}$ (Nujol)/cm$^{-1}$ 3500–3300, 3067, 2920, 2851, 1591, 1549, 1451, 1099 and 756; NMR $\delta_H$ (400 MHz, CDCl$_3$) 1.11–1.30 (4H, m), 1.51–1.54 (2H, m), 1.63–1.64 (1H, m), 1.71–1.82 (4H, m), 2.01–2.04 (1H, m), 2.70 (3H, s), 5.13 (1H, t, J 4.0 Hz), 7.33 (1H, s), 7.42 (1H, t, J 7.0 Hz), 7.63 (1H, t, J 8.3 Hz), 7.89 (1H, d, J 8.5 Hz) and 7.98 (1H, d, J 7.5 Hz).

Example 79

2-Benzylamino-α-cyclohexyl-4-quinolinemethanol

Isolated as a white solid, (151 mg, 88%): mp 122.5–123.1° C.; IR $v_{max}$ (Nujol)/cm$^{-1}$ 3347, 2925, 2854, 1615, 1525, 1496, 1453, 1378 and 768; NMR $\delta_H$ (400 MHz, CDCl$_3$) 1.07–1.27 (5H, m), 1.53–1.71 (6H, m), 1.99–2.22 (1H, s), 4.69 (2H, d, J 5.8 Hz), 5.07 (1H, d, J 5.1 Hz), 5.12–5.37 (1H, s), 6.71 (1H, s), 7.19–7.40 (6H, m), 7.52 (1H, t, J 7.0 Hz), and 7.71–7.74 (2H, m).

Example 80

2-Cyclohexylaminoa-phenyl-4-quinolinemethanol hydrochloride

Isolated as a white solid, (65 mg, 18%): mp 194–195° C.; IR $v_{max}$ (Nujol)/cm$^{-1}$ 3500–3300,2924, 2855, 1657, 1618, 1589, 1456 and 1378; NMR $\delta_H$ (400 MHz, ?) 1.19–1.57 (5H, m), 1.64–1.69 (1H, m), 1.78–1.82 (2H, m), 2.02–2.05 (2H, m), 4.24–4.26 (1H, m), 6.29 (1H, s), 7.24–7.52 (7H, m), 7.68 (1H, t, J 7.2 Hz), 7.90 (1H, d, J 8.2 Hz), 8.20 (1H, d, J 8.1 Hz) 9.55 (1H, d, J 8.1 Hz) and 12.95 (1H, s).

The following synthetic intermediate was prepared using Method I from the appropriate 2-bromoquinoline.

4-Bromo-2-methoxy-8-methylquinoline

Isolated as a white solid, (1.46 g, 83%): mp 98–99° C.; IR $v_{max}$ (Nujol)/cm$^{-1}$ 3101, 3070, 2925, 2855, 1657, 1598, 1576, 1327, 1232 and 752; NMR $\delta_H$ (400 MHz, CDCl$_3$) 2.71 (3H, s), 4.07 (3H, s), 7.25 (1H, s), 7.35 (1H, t, J 7.5 Hz), 7.54 (1H, d, J 7.1 Hz) and 7.95 (1H, d, J 7.7 Hz).

Method J

4-Bromo-N,N-dibenzyl-2-quinolineamine

A solution of 2-amino-4-bromoquinoline (244 mg, 1.09 mmol) in THF (5 mL) at 0° C. was treated with NaH (96 mg, 60% dispersion in oil, 2.4 mmol), stirred for 30 min, treated with benzyl bromide (0.335 mL, 2.4 mmol), stirred at room temperature for 3 days, poured into water (30 mL), extracted with EtOAc (2×10 mL), dried (MgSO$_4$), concentrated in vacuo, purified by chromatography [SiO$_2$; heptane-EtOAc (10:1)] and the resulting solid recystallised (MeOH) to give the product (407 mg, 99%) as a white crystalline solid: IR $\nu_{max}$ (Nujol)/cm$^{-1}$ 3059, 3020, 2955, 2925, 2854, 1609, 1592, 1542, 1498, 1455, 1426 and 1358; NMR $\delta_H$ (400 MHz, CDCl$_3$) 4.89 (4H, s), 7.15 (1H, s), 7.20–7.68 (11H, m),7.56 (1H, t, J 7.0 Hz), 7.69 (1H, d, J 8.7 Hz) and 7.94 (1H, d, J 8.4 Hz).

Method K

Example 81

1-(2,8-Bis(trifluoromethyl)-4-quinolinyl)-4-hydroxybutanol

A solution of 1-(2,8-bis(trifluoromethyl)-4-quinolinyl)-4-hydroxybutanone (748 mg, 2.13 mmol) in EtOH (4 mL) at 0° C. was treated with a solution of NaBH$_4$ (81 mg, 2.13 mmol) in water (0.2 mL), stirred at 0° C. for 30 min, poured into water (15 mL), extracted with EtOAc (2×10 mL),dried (MgSO$_4$), concentrated in vacuo and purified by chromatography [SiO$_2$; EtOAc-heptane (2:1)] to give the title compound (618 mg, 82%) as a colourless oil; IR $\nu_{max}$ (Nujol)/cm$^{-1}$ 3600–3200, 2938, 2885, 1604,1588, 1430, 1310, 1189, 1144 and 1110; NMR $\delta_H$ (400 MHz, CDCl$_3$) 1.81–1.91 (3H, m), 2.08–2.17 (1H, m), 2.45–2.70 (2H, br s),3.75–3.78 (1H, m), 3.80–3.88 (1H, m), 5.52 (1H, d, J 8.0 Hz), 7.71 (1H, t, J 7.9 Hz), 8.08 (1H, s), 8.15 (1H, d, J 7.2 Hz) and 8.23 (1H, d, J 8.7 Hz).

The following compounds (Examples 82–83) were prepared by Method J using the appropriate ketones.

Example 82

1-(2,8-Bis(trifluoromethyl)-4-quinolinyl)-5-hydroxypentanol

Isolated as a white solid, (1.03 g, 94%): mp 120.6–120.9° C.; IR $\nu_{max}$ (Nujol)/cm$^{-1}$ 3322, 3200, 2924,2854, 1604, 1461, 1376, 1317, 1105 and 770; NMR $\delta_H$ (400 MHz, DMSOd-$_6$) 1.35–1.50 (4H, m), 1.62–1.71 (1H, m), 1.73–1.79 (1H,m), 3.33–3.37 (2H, m), 4.36 (1H, t, J 5.1 Hz), 5.48 (1H, t, J 4.0 Hz), 5.89 (1H, d, J 4.0 Hz), 7.92 (1H, t, J 7.8 Hz), 8.10 (1H, s), 8.35 (1H, d, J 7.5 Hz) and 8.63 (1H, d, J 8.1 Hz); Anal. Calcd for C$_{16}$H$_{15}$F$_6$NO$_2$: C, 52.32; H, 4.12; N, 3.81. Found: C, 52.20; H, 4.23; N, 3.76.

Example 83

2-Chloro-α-phenyl-4-quinolinemethanol

Isolated as a white solid, (32 mg, 90%): mp 144–146° C.; IR $\nu_{max}$ (Nujol)/cm$^{-1}$ 3230, 2925, 2855, 1584, 1564, 1456, 1314, 1163, 1106, 1083 and 1070; NMR $\delta_H$ (400 MHz, CDCl$_3$) 2.51 (1H, d, J 3.5 Hz), 6.43 (1H, d, J 3.0 Hz), 7.30–7.37 (5H, m), 7.41–7.45 (1H, m), 7.63–7.66 (1H, m), 7.77 (1H, s), 7.80–7.83 (1H, m) and 8.00–8.02 (1H, d, J 8.5 Hz); Anal. Calcd for C$_{16}$H$_{12}$ClNO: C, 71.25; H, 4.48; N, 5.19. Found: C, 70.95; H, 4.57; N, 5.01.

Method L

Example 84

1-(2,8-Bis(trinfluoromethyl)-4-quinolinyl)-2-fluoro-2-methylpropanol

A solution of 2,8-bis(trifluoromethyl)-4-(3,3-dimethyl-2-oxiranyl)quinoline (335 mg, 1.0 mmol) in CH$_2$Cl$_2$ (5 mL) at 0° C. was reated with BF$_3$ Et$_2$O (123 μL, 1.0 mmol), stirred at 0° C. for 30 min, poured into dilute NaHCO$_3$ (20 mL), extracted with CH$_2$Cl$_2$ (2×10 mL), dried (MgSO$_4$), concentrated in vacuo and purified by chromatography [SiO$_2$; heptane-EtOAc (5:1)] to give the title compound (118 mg, 33%) as a white solid: m.p. 98.2–99° C.; IR $\nu_{max}$ (Nujol)/cm$^{-1}$ 3466, 2924, 2854, 1604, 1587, 1519, 1462, 1377 and 1319; NMR $\delta_H$ (400 MHz, CDCl$_3$) 1.33 (3H, d, J 22.6 Hz), 1.51 (3H, d, J 22.0 Hz), 2.70 (1H, d, J 2.7 Hz), 5.63 (1H, td J 2.9 Hz), 7.73 (1H, t, J 8.0 Hz), 8.08 (1H, s), 8.17 (1H, d, J 7.4 Hz) and 8.38 (1H, d, J8.7 Hz); M/Z 356 (M+H)$^+$.

Method M

Example 85

4(1-Cyclohexyl-1-hydroxymethyl)-8-methyl-2-quinolinecarboxylic acid

A solution of isobutyl 4-(α-hydroxycyclohexylmethyl)-8-methylquinoline-2-carboxylate (153 mg, 0.43 mmol) in MeOH (2 mL) was treated with 1M-NaOH solution (2 mL), stirred for 16 h, concentrated in vacuo, diluted with water (2 mL), washed with ether (2×2 mL), acidified with 1M-HCl (2 mL), extracted with EtOAc (3×2 mL), and the combined organic phase dried (MgSO4) and concentrated in vacuo to give the title compound (65 mg, 50%) as a cream solid: IR $\nu_{max}$ (Nujol)/cm$^{-1}$ 3600–3400, 3287, 2924, 2854, 1742, 1462, 1378, 1318, 1291 and 763; NMR $\delta_H$ (400 MHz, CDCl$_3$) 1.03–1.30 (5H, m), 1.45–1.67 (6H, m), 2.80 (3H, s), 5.20 (1H, t, J 4.5 Hz), 5.57 (1H, d, J 4.1 Hz), 7.62 (1H, t, J 7.8 Hz), 7.71 (1H, d, J 7.1), 8.09 (1H, d, J 8.6 Hz), 8.19 (1H, s) and 13.15–13.31 (1H, br s); Anal. Calcd for C$_{18}$H$_{21}$NO$_3$.0.25 H$_2$O: C, 71.15; H, 7.13; N, 4.61. Found: C, 71.23; H, 7.11; N, 4.54.

Method N

Example 86

α-Cyclohexyl-2-hydroxy-4-quinolinemethanol

A solution of 2-bromo-α-cyclohexyl-4-quinolinemethanol (100 mg, 0.31 mmol) in dioxan (1 mL) was treated with 1-M HCl, stirred at room temperature for 16 h, refluxed for 24 h, cooled, diluted with water (5 mL), the resulting solid filtered and dried under vacuum to give the title compound (58 mg, 73%) as a white solid: mp>250° C.; IR $\nu_{max}$ (Nujol)/cm$^{-1}$ 3451, 2956, 2924, 2854, 1649, 1546, 1437, 1103, 886 and 760; NMR $\delta_H$ (400 MHz, DMSO-d$_6$) 1.07–1.29 (5H, m), 1.53–1.69 (6H, m), 4.77 (1H, t, J 4.5 Hz), 5.38 (1H, d, J 4.6 Hz), 6.50 (1H, s), 7.18 (1H, t, J 7.0 Hz), 7.34 (1H, d, J 7.6 Hz), 7.49 (1H, t, J 7.0 Hz), 7.84 (1H, d, J 7.6 Hz) and 11.64 (1H, s); M/Z 258 (M+H)$^+$.

The following compounds (Examples 87–88) were prepared by Method N from the appropriately substituted 2-bromoquinoline:

Example 87

α-Cyclobexyl-2-hydroxy-8-methyl-4-quinolinemethanol

Isolated as a white solid, (131 mg, 90%): NMR $\delta_H$ (400 MHz, DMSO-d$_6$) 1.05–1.17 (4H, m), 1.23–1.37 (1H, m), 1.55–1.69 (6H, m), 3.34 (3H, s), 4.80 (1H, t, J 4.0 Hz), 5.37 (1H, d, J 4.5 Hz), 6.54 (1H, s), 7.10 (1H, t, J 7.8 Hz), 7.35 (1H, d, J 7.6 Hz), 7.69 (1H, d, J 8.1 Hz), and 10.69 (1H, s); M/Z 272 (M+H)$^+$.

Example 88

2-Hydroxy-8-methyl-α-(2-pyridyl)-4-quinolinemethanol

Isolated as a cream solid, (300 mg, 43%): mp 215° C. (dec); IR $v_{max}$ (Nujol)/cm$^{-1}$ 2924, 2854, 1651, 1599, 1573, 1466, 1379, 1062, 780, 754 and 744; NMR $\delta_H$ (400 MHz, DMSO-d$_6$) 3.19 (1H, d, J 5.1 Hz), 3.34 (3H, s), 6.11 (1H, d, J 4.6 Hz), 6.41 (1H, d, J 4.7 Hz), 6.76 (1H, s), 6.99 (1H, t, J 7.8 Hz), 7.26–7.29 (2H, m), 7.58 (1H, d, J 8.0 Hz), 7.70 (1H, d, J 8.0 Hz), 7.81 (1H, dt, J 7.6, 1.8 Hz), 8.49 (1H, d, J 5.6 Hz) and 10.80 (1H, s); Anal. Calcd for C$_{16}$H$_{14}$N$_2$O$_2$.0.15 H$_2$O: C, 71.44; H, 5.36; N, 10.41. Found: C, 71.62; H, 5.30; N, 10.38; M/Z 267 (M+H)$^+$.

Method O

Example 89

α-Cyclohexyl-2-methanesulphonyl-4-quinolinemethanol

A solution of α-cyclohexyl-2-methylthio-4-quinolinemethanol (214 mg, 0.75 mmol) in CH$_2$Cl$_2$ (5 mL) was treated with m-chloroperbenzoic acid (60%, 0.22 mg, 0.75 mmol), stirred at room temperature for 1 h, diluted with EtOAc (5 mL), washed (dil. NaHCO$_3$), dried (MgSO$_4$), concentrated in vacuo and purified by chromatography [SiO$_2$; heptane-EtOAc (2:1)] to give the title compound (123 mg, 66%) as a white solid: mp 83° C.; NMR $\delta_H$ (400 MHz, CDCl$_3$) 0.99–1.38 (5H, m), 1.46–1.88 (7H, m), 2.17–2.20 (1H, m), 3.37 (3H, s), 5.30 (1H, d, J 6.4 Hz), 7.71 (1H, t, J 7.0 Hz), 7.83 (1H, t, J 8.3 Hz), 8.13 (1H, d, J 8.5 Hz) and 8.23 (1H, d, J 8.3 Hz).

Method P

Example 90

α,α-Diphenyl-2-hydroxy-4-quinolinemethanol

A solution of methyl 2-hydroxy-4-quinolinecarboxylate (406 mg, 2 mmol) in THF (20 mL) at 0° C. was treated with a solution of phenyl lithium (1.8-M in THF, 2.3 mL, 4.2 mmol), stirred at room temperature for 2 h, poured into water (100 mL), the resulting precipitate filtered and dried to give the title compound (636 mg, 97%) as a cream solid: mp>350° C.; IR $v_{max}$ (Nujol)/cm$^{-1}$ 3550–3300,3085, 3059, 2924, 2854, 1652, 1461, 1377, 759, 750 and 698; NMR $\delta_H$ (400 MHz, ?) 5.66 (1H, s), 6.88 (1H, t, J 7.6 Hz), 7.28–7.39 (11H, m), 7.47 (1H, t, J 7.5 Hz), 7.66 (1H, d, J 8.6 Hz), 7.81 (1H, d, J 7.6 Hz) and 11.63–11.88 (1H, s); M/Z 328 (M+H)$^+$.

The following compound (Example 91) was prepared from 2-phenylquinoline-4-carboxaldehyde by Method P.

Example 91

2,α-Diphenyl-4-quinolinemethanol

Isolated as a white solid, (240 mg, 36%): mp 111–112° C.; IR $v_{max}$ (Nujol)/cm$^{-1}$ 3221, 2924, 1594, 1457, 1377, 1062 and 696; NMR $\delta_H$ (400 MHz, CDCl$_3$) 2.65 (1H, br s), 6.50 (1H, d, J 3.0 Hz), 7.25–7.54 (10H, m), 7.65 (1H, m), 7.85 (1H, d, J 8.0 Hz) and 8.17–8.20 (3H, m); Anal. Calcd for C$_{22}$H$_{17}$NO: C, 84.86; H, 5.50; N, 4.50. Found: C, 84.62; H, 5.49; N, 4.28.

Method Q

Example 92

4-(2-Benzofuranyl)-2,8-bis(trifluoromethyl)quinoline

A solution of 4-bromo-2,8-bis(trifluoromethyl)quinoline (500 mg, 1.45 mmol) in dry dimethoxyethane (10 mL) was treated with tetrakis(triphenylphosphine)palladium (2.3 mg, 10 mol %), stirred for 10 min, treated with benzofuran-2-boronic acid (235 mg, 1.45 mmol) and 2-M Na$_2$CO$_3$ solution (1.45 mL, 2.9 mmol) then refluxed for 2 h. The mixture was cooled, treated with water (10 mL), extracted with EtOAc (3×20 mL), the organic phase was washed with brine (20 mL), dried (MgSO$_4$), concentrated in vacuo and the resulting yellow solid recrystallised from heptane to give the title compound (351 mg, 64%) as an off-white crystalline solid: mp 129–130° C.; IR $v_{max}$ (Nujol)/cm$^{-1}$ 2924, 1592, 1463, 1314, 1145, 1116, 1010, 749 and 691; NMR $\delta_H$ (400 MHz, CDCl$_3$) 7.35 (1H, t, J 7.1 Hz), 7.42–7.47 (2H, m), 7.65 (1H, d, J 7.5 Hz), 7.73 (1H, d, J 8.0 Hz), 7.80 (1H, t, J 7.9 Hz), 8.19–8.23 (2H, m) and 8.86 (1H, d, J 9.0 Hz).

The following compound (Example 93) was prepared by Method Q using the appropriate boronic acid.

Example 93

2,8-Bis(trifluoromethyl)-4-(2-furanyl)quinoline

Isolated as a pale yellow crystalline solid, (266 mg, 55%): mp 82–83° C.; IR $v_{max}$ (Nujol)/cm$^{-1}$ 2925, 1594, 1309, 1130, 1007, 748 and 694; NMR $\delta_H$ (400 MHz, CDCl$_3$) 6.68 (1H, dd, J 3.5, 2.0 Hz), 7.08 (1H, d, J 3.5 Hz), 7.72–7.76 (2H, m), 8.01 (1H, s), 8.17 (1H, d, J 7.0 Hz), and 8.79 (1H, d, J 8.1 Hz).

Method R

Example 94

2,8-Bis(trifluoromethyl)-4-(tetrahydrofuran-2-yl)quinoline

A solution of 1-(2,8-bis(trifluoromethyl)-4-quinolinyl)-4-hydroxybutanol (176 mg, 0.5 mmol) in CH$_2$Cl$_2$ (5 mL) was treated with p-toluenesulphonyl chloride (102 mg, 0.55 mmol) and triethylamine (0.084 mL, 0.6 mmol) and stirred at room temperature for 16 h. The mixture was poured into saturated NaHCO$_3$ solution (10 mL), extracted with CH$_2$Cl$_2$ (2×10 mL) and the combined organic phase dried (MgSO$_4$), concentrated in vacuo, purified by chromatography [SiO$_2$, heptane-EtOAc (95:5)] and the resulting solid triturated with cold hexane and filtered to give the title compound (111 mg, 66%) as a white solid: mp 61.0–61.7° C.; IR $v_{max}$ (Nujol)/cm$^{-1}$ 3096, 2924, 2854, 1603, 1585, 1516, 1463, 1431, 1308, 1178, 1100, 1086 and 775; NMR $\delta_H$ (400 MHz, CDCl$_3$) 1.79–1.86 (1H, m), 2.00–2.16 (2H, m), 2.63–2.71 (1H, m), 4.08 (1H, q, J 7.3 Hz), 4.24–4.29 (1H, m), 5.63 (1H, t, J 7.3 Hz), 7.72 (1H, t, J 7.7 Hz), 7.99 (1H, s), and 8.14–8.18 (2H, m).

The following compound (Example 95) was prepared by Method R using the appropriate alcohol.

Example 95

2,8-Bis(trifluoromethyl)-4-(2H-tetrahydropyran-2-yl)quinoline

Isolated as a white crystalline solid, (140 mg, 40%): mp 134.7–135.2° C.; IR $v_{max}$ (Nujol)/cm$^{-1}$ 2925, 2854, 1600, 1584, 1466, 1427, 1308, 1282, 1189, 1166, 1131, 1107, 1086 and 774; NMR $\delta_H$ (400 MHz, CDCl$_3$) 1.56–1.89 (4H, m), 2.00–2.09 (2H, m), 3.76 (1H, dt, J 11.6, 2.5 Hz), 4.27–4.30 (1H, m), 5.08 (1H, dd, J 11.5, 2.1 Hz), 7.71 (1H, t, J 8.1 Hz), 8.00 (1H, s), 8.14 (1H, d, J 7.1 Hz) and 8.25 (1H, d, J 8.5 Hz).

Method S

Example 96

2,8-Bis(trinfluoromethyl)-4-(2H-tetrahydropyran-2-yl)quinoline

A solution of 1-(2,8-bis(trifluoromethyl)-4-quinolinyl)-2-bromo-2-methylpropanone (1.46 g, 3.52 mmol) in EtOH (12 mL) and ethoxyethanol (4.2 mL) at 0° C. was treated with a solution of NaBH$_4$ (135 mg, 3.57 mmol) in water (0.9 mL), stirred at room temperature for 1.5 h, treated with KOH (151 mg, 2.69 mmol), stirred at room temperature for 30 min, poured into water (50 mL), extracted with EtOAc (2×25 mL), dried (MgSO$_4$), concentrated in vacuo, purified by chromatography [SiO$_2$; heptane-EtOAc (2:1)] and recrystallised (heptane) to give the product (996 mg, 84%) as white needles: m.p. 76.0–76.6° C.; IR $\nu_{max}$ (Nujol)/cm$^{-1}$ 3249, 2955, 2924, 2854, 1742, 1657, 1604, 1585, 1459 and 1304; NMR $\delta_H$ (400 MHz, CDCl$_3$) 1.04 (3H, s), 1.71 (3H, s), 4.33 (1H, s), 7.79 (1H, t, J 7.9 Hz), 7.79 (1H, t, J 7.9 Hz), 7.82 (1H, s) and 8.21 (2H, d, J 8.1 Hz).

Method T 2,4-Dibromo-8-methylquinoline

A mixture of malonic acid (3.12 g, 30 mmol) and POBr$_3$ (20 mL) at 60° C. was treated portionwise with o-toluidine (4.06 mL, 38 mmol), heated at 130° C. for 3 h, cooled, poured into ice, and the resulting solid filtered, purified by chromatography [SiO$_2$; heptane-EtOAc (9:1)] and recrystallised to give the product (1.61 g, 19%) as a white solid: IR $\nu_{max}$ (Nujol)/cm$^{-1}$ 2923, 2854, 1559, 1480, 1460, 1379, 1114,869, 847, 798, 775 and 758; NMR $\delta_H$ (400 MHz, CDCl$_3$) 2.76 (3H, s), 7.54 (1H, m), 7.62 (1H, d, J 7.0 Hz), 7.83 (1H, s) and 8.00 (1H, d, J 8.6 Hz).

Method U 2,8-Bis(trifluoromethyl)-3-methyl-4-quinolinol

To polyphosphoric acid (101 g) heated to 75° C. was added ethyl 2-methyl-4,4,4-trifluoroacetoacetate (10.0 g, 50.5 mmol). 2-Trifluoromethylaniline (6.0 mL, 48.1 mmol) was added dropwise and the reaction mixture heated to 120° C. for 6 h, cooled in ice and treated with water. The cream precipitate was filtered and washed with water and heptane to afford the product (11.4 g, 80%) as a white solid: mp 116.2–116.8° C.; IR $\nu_{max}$ (Nujol)/cm$^{-1}$ 3440, 2924, 2854, 1624, 1612, 1584, 1458, 1330, 1226, 1142, 1109; NMR $\delta_H$ (400 MHz, CDCl$_3$) 2.29 (3H, s), 7.47 (1H, t, J 7.6 Hz), 7.98 (1H, d, J 7.6 Hz), 8.60 (1H, d, J 7.4 Hz).

The following compound was prepared by Method U from the appropriately substituted aniline and acetoacetate ester.

8-Ethyl-2-trifluoromethyl-4-quinolinol

Isolated as a pink solid, (10.61 g, 37%): mp 157–159° C.; IR $\nu_{max}$ (Nujol)/cm$^{-1}$ 3292, 2925, 1593, 1461, 1291, 1164, 829 and 516; NMR $\delta_H$ (400 MHz, CDCl$_3$) 1.28 (3H, t, J 7.5 Hz), 3.16 (2H, q, J 7.5 Hz), 7.16 (1H, s), 7.58 (1H, t, J 8.5 Hz), 7.69 (1H, d, J 6.0 Hz) and 8.07 (1H, d, J 8.4 Hz); Anal. Calcd for C$_{12}$H$_{10}$F$_3$NO: C, 59.75; H, 4.18; N, 5.80. Found: C, 59.79; H, 4.33; N, 5.77.

Method V 2,8-Bis(trifluoromethyl)-4-bromo-3-methylquinoline

A solution of 2,8-bis(trifluoromethyl)-3-methyl-4-quinolinol (5.9 g, 20 mmol) in toluene (20 mL) was treated with POBr$_3$ (6.0 g, 21 mmol), heated to reflux for 30 min, cooled in ice, quenched with water and extracted with EtOAc (2×50 mL). The combined extracts were dried (MgSO$_4$), concentrated in vacuo and the resulting brown solid purified by flash chromatography [SiO$_2$; heptane] to give the product (5.8 g, 81%) as a white crystalline solid: mp 81.9–82.3° C.; IR $\nu_{max}$ (Nujol)/cm$^{-1}$ 2955, 2924, 2854, 1574, 1465, 1364, 1299, 1281, 1213, 1189, 1141; NMR $\delta_H$ (400 MHz, CDCl$_3$) 2.77 (3H, s), 7.78 (1H, t, J 8.1 Hz), 8.14 (1H, d, 7.4 Hz), 8.49 (1H, d, J 8.5 Hz).

The following novel compounds were prepared by Method V from the appropriately substituted 4-quinolinols:

4-Bromo-8-methoxy-2-trinfluoromethylquinoline

Isolated as a white solid, (4.2 g, 42%): mp 81–82° C.; IR $\nu_{max}$ (Nujol)/cm$^{-1}$ 2925, 2855, 1611, 1561, 1498, 1481, 1440, 1412, 1366, 1340, 1280, 1266, 1213, 1177, 1131, 1106 and 1004; NMR $\delta_H$ (400 MHz, CDCl$_3$) 4.11 (3H, s), 7.20 (1H, d, J 7.0 Hz), 7.70 (1H, t, J 8.0 Hz), 7.83 (1H, d, J 8.0 Hz) and 8.05 (1H, s).

4-Bromo-8-methyl-2-trifluoromethylquinoline

Isolated as a waxy white solid, (3.68 g, 72%): IR $\nu_{max}$ (Nujol)/cm$^{-1}$ 2925, 1467, 1337, 1146, 1113 and 764; NMR $\delta_H$ (400 MHz, CDCl$_3$), 2.82 (3H, s), 7.60–7.69 (2H, m), 7.99 (1H, s) and 8.08 (1H, d, J 7.5 Hz).

4-Bromo-8-ethyl-2-trifluoromethylquinoline

Isolated as a pale yellow oil, (3.08 g, 49%): IR $\nu_{max}$ (Nujol)/cm$^{-1}$ 2971, 1468, 1338, 1143, 879 and 765; NMR $\delta_H$ (400 MHz, CDCl$_3$), 1.36 (3H, t, J 7.5 Hz), 3.31 (2H, q, J 7.5 Hz) 7.64–7.70 (2H, m), 7.98 (1H, s) and 8.08 (1H, dd, J 7.9, 1.9 Hz).

4-Bromo-2,8-dimethylquinoline

Isolated as a white solid, (11.5 g, 82%): mp 74–75° C.; IR $\nu_{max}$ (Nujol)/cm$^{-1}$ 2957, 2855, 1612, 1586, 1566, 1488, 1464, 1403, 1374, 1304, 1210, 1162 and 1037; NMR $\delta_H$ (400 MHz, CDCl$_3$) 2.72 (3H, s), 2.79 (3H, s), 7.44 (1H, dd, J 8.5, 7.0 Hz), 7.56 (1H, d, J 7.0 Hz), 7.59 (1H, s) and 7.98 (1H, d, J 8.5 Hz); Anal. Calcd for C$_{11}$H$_{10}$BrN: C, 55.96; H, 4.27; N, 5.93. Found: C, 56.00; H, 4.29; N, 5.84.

Adenosine Receptor Binding

Binding Affinities at hA$_{2A}$ Receptors

The compounds were examined in an assay measuring in vitro binding to human adenosine A$_{2A}$ receptors by determining the displacement of the adenosine A$_{2A}$ receptor selective radioligand [$^3$H]-CGS 21680 using standard techniques. The results are summarised in Table 1.

TABLE 1

| | Ki (nM) |
|---|---|
| Example 1 | 1700 |
| Example 2 | 1546 |
| Example 3 | 954 |
| Example 4 | 1124 |
| Example 5 | 1026 |
| Example 7 | 852 |
| Example 10 | 1747 |
| Example 11 | 1357 |
| Example 12 | 1898 |
| Example 16 | 1789 |
| Example 18 | 1191 |
| Example 19 | 1735 |
| Example 20 | 649 |
| Example 21 | 743 |
| Example 22 | 1922 |
| Example 23 | 701 |
| Example 26 | 1111 |
| Example 27 | 1132 |
| Example 28 | 574 |
| Example 29 | 965 |
| Example 31 | 1772 |
| Example 32 | 1069 |
| Example 47 | 1066 |
| Example 51 | 1518 |
| Example 74 | 1633 |

Evaluation of Potential Anti-Parkinsonianactivity In vivo

Haloperidol-induced Hypolocomotion Model

It has previously been demonstrated that adenosine antagonists, such as theophylline, can reverse the behavioural depressant effects of dopamine antagonists, such as haloperidol, in rodents (Mandhane S. N. et al., Adenosine $A_2$ receptors modulate haloperidol-induced catalepsy in rats. *Eur. J. Pharmacol.* 1997, 328, 135–141). This approach is also considered a valid method for screening drugs with potential antiparkinsonian effects. Thus, the ability of novel adenosine antagonists to block haloperidol-induced deficits in locomotor activity in mice can be used to assess both in vivo and potential antiparkinsonian efficacy.

Method

Female TO mice (25–30 g) obtained from TUCK, UK, are used for all experiments. Animals are housed in groups of 8 [cage size–40 (width)×40 (length)×20 (height)cm] under 12 hr light/dark cycle (lights on 08:00 hr), in a temperature (20±2° C.) and humidity (55±15%) controlled environment. Animals have free access to food and water, and are allowed at least 7 days to acclimatize after delivery before experimental use.

Drugs

Liquid injectable haloperidol (1 ml Serenance ampoules from Baker Norton, Harlow, Essex, each containing haloperidol BP 5 mg, batch # P424) are diluted to a final concentration of 0.02 mg/ml using saline. Test compounds are typically prepared as aqueous suspensions in 8% Tween. All compounds are administered intraperitoneally in a volume of 10 ml/kg.

Procedure 1.5 hours before testing, mice are administered 0.2 mg/kg haloperidol, a dose that reduces baseline locomotor activity by at least 50%. Test substances are typically administered 5–60 minutes prior to testing. The animals are then placed individually into clean, clear polycarbonate cages [20 (width)×40 (length)×20 (height) cm, with a flat perforated, Perspex lid]. Horizontal locomotor activity is determined by placing the cages within a frame containing a 3×6 array of photocells linked to a computer, which tabulates beam breaks. Mice are left undisturbed to explore for 1 hour, and the number of beams breaks made during this period serves as a record of locomotor activity which is compared with data for control animals for statistically significant differences. In this model, Example 86, administered intraperitoneally at a dose of 10 mg/kg, significantly reversed haloperidol-induced hypolocomotion.

6-OHDA Model

Parkinson's disease is a progressive neurodegenerative disorder characterised by symptoms of muscle rigidity, tremor, paucity of movement (hypokinesia), and postural instability. It has been established for some time that the primary deficit in PD is a loss of dopaminergic neurones in the substantia nigra which project to the striatum, and indeed a substantial proportion of striatal dopamine is lost (ca 80–85%) before symptoms are observed. The loss of striatal dopamine results in abnormal activity of the basal ganglia, a series of nuclei which regulate smooth and well co-ordinated movement (Blandini F. et al., Glutamate and Parkinson's Disease. *Mol. Neurobiol.* 1996, 12, 73–94). The neurochemical deficits seen in Parkinson's disease can be reproduced by local injection of the dopaminergic neurotoxin 6-hydroxydopamine into brain regions containing either the cell bodies or axonal fibres of the nigrostriatal neurones.

By unilaterally lesioning the nigrostriatal pathway on only one-side of the brain, a behavioural asymmetry in movement inhibition is observed. Although unilaterally-lesioned animals are still mobile and capable of self maintenance, the remaining dopamine-sensitive neurones on the lesioned side become supersenstive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has proven to be a sensitive model to predict drug efficacy in the treatment of Parkinson's Disease.

Animals

Male Sprague-Dawley rats, obtained from Charles River, were used for all experiments. Animals were housed in groups of 5 under 12 hr light/dark cycle (lights on 08:00 hr), in a temperature (20±2° C.) and humidity (55±15%) controlled environment. Animals had free access to food and water, and allowed at least 7 days to acclimatize after delivery before experimental use.

Drugs

Ascorbic acid, desipramine, 6-OHDA and apomorphine were obtained from Sigma-Aldrich, Poole, UK. 6-OHDA was freshly prepared as a solution in 0.2% ascorbate at a concentration of 4 mg/mL prior to surgery. Desipramine was dissolved in warm saline, and administered in a volume of 1 ml/kg. Apomorphine was dissolved in 0.02% ascorbate and administered in a volume of 2 mL/kg. Test compounds were suspended in 8% Tween and injected in a volume of 2 mL/kg.

Surgery 15 minutes prior to surgery, animals were given an intraperitoneal injection of the noradrenergic uptake inhibitor desipramine (25 mg/kg) to prevent damage to non-dopamine neurones. Animals were then placed in an anaesthetic chamber and anaesthetised using a mixture of oxygen and isoflurane. Once unconscious, the animals were transferred to a stereotaxic frame, where anaesthesia was maintained through a mask. The top of the animal's head was shaved and sterilised using an iodine solution. Once dry, a 2 cm long incision was made along the midline of the scalp and the skin retracted and clipped back to expose the skull. A small hole was then drilled through the skill above the injection site. In order to lesion the nigrostriatal pathway, the injection cannula was slowly lowered to position above the right medial forebrain bundle at −3.2 mm anterior posterior, −1.5 mm medial lateral from bregma, and to a depth of 7.2 mm below the duramater. 2 minutes after lowing the cannula, 2 μof 6-OHDA was infused at a rate of 0.5 μL/min over 4 minutes, yielding a final dose of 8 μg. The cannula was then left in place for a further 5 minutes to facilitate diffusion before being slowly withdrawn. The skin was then sutured shut using Ethicon W501 Mersilk, and the animal removed from the strereotaxic frame and returned to its homecage. The rats were allowed 2 weeks to recover from surgery before behavioural testing.

Apparatus

Rotational behaviour was measured using an eight station rotameter system provided by Med Associates, San Diego, USA. Each station was comprised of a stainless steel bowl (45 cm diameter×15 cm high) enclosed in a transparent Plexiglas cover running around the edge of the bowl, and extending to a height of 29 cm. To assess rotation, rats were placed in cloth jacket attached to a spring tether connected to optical rotameter positioned above the bowl, which assessed movement to the left or right either as partial (45°) or full (360°) rotations. All eight stations were interfaced to a computer that tabulated data.

Procedure

To reduce stress during drug testing, rats were initially habituated to the apparatus for 15 minutes on four consecutive days. On the test day, rats were given an intraperitoneal injection of test compound 30 minutes prior to testing. Immediately prior to testing, animals were given a subcutaneous injection of a subthreshold dose of apomorphine, then placed in the harness and the number of rotations recorded for one hour. The total number of full contralatral rotations during the hour test period served as an index of antiparkinsonian drug efficacy.

What is claimed is:

1. A method of treating or preventing movement disorders, comprising administering to a subject in need thereof an effective amount of a compound of formula I:

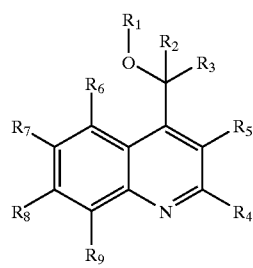

wherein:

$R_1$ is hydrogen or alkyl;

$R_2$ and $R_3$ are independently selected from the group consisting of hydrogen, alkyl, aryl and 4, 5, 6, 7 or 8 membered unbridged saturated and partially unsaturated heterocyclic rings containing one or more heteroatoms selected from the group consisting of O, S and N, or together form a 3, 4, 5, 6 or 7 membered saturated or partially-unsaturated carbocyclic ring or a 3, 4, 5, 6, 7 or 8 membered saturated or partially unsaturated heterocyclic ring containing one or more heteroatoms selected from the group consisting of O, S and N;

or $R_1$ and $R_2$ or $R_3$ together form a 3, 4, 5, 6, 7 or 8 membered oxygen-containing saturated or partially unsaturated heterocyclic ring optionally containing one or more additional heteroatoms selected from the group consisting of O, S and N;

or $R_1$ and $R_2$ and $R_3$ together form a 4, 5, 6, 7 or 8 membered oxygen-containing partially unsaturated or aromatic heterocyclic ring optionally containing one or more additional heteroatoms selected from the group consisting of O, S and N in which $R_2$ and $R_3$ together form a double bond;

wherein said carbocyclic ring or said heterocyclic ring when partially unsaturated or aromatic may be fused to an aryl ring; and $R_4$, $R_5$, $R_6$, $R_7$, $R_8$ and $R_9$ are independently selected from the group consisting of hydrogen, alkyl; aryll 4, 5, 6, 7 or 8 membered saturated and partially unsaturated heterocyclic rings containing one or more heteroatoms selected from the group consisting of O, S, and N; hydroxy; halogen, nitro, cyano, alkoxy, aryloxy, $COR_{10}$, $OCOR_{10}$, $CO_2R_{10}$, $SR_{10}$, $SOR_{10}$, $SO_2R_{10}$, $SO_2NR_{10}R_{11}$, $CONR_{10}R_{11}$, $CONR_{10}NR_{11}R_{12}$, $OCONR_{10}R_{11}$, $NR_{10}R_{11}$, $NR_{10}COR_{11}$, $NR_{10}CONR_{11}R_{12}$, $NR_{10}CO_2R_{11}$, $NR_{10}SO_2R_{11}$, $CR_{10}NOR_{11}$, $NR_{10}CONR_{11}NR_{12}R_{13}$, $NR_{10}NR_{11}CO_2R_{12}$, $NR_{10}NR_{11}CONR_{12}R_{13}$, $NR_{10}NR_{11}COR_{12}$, $NR_{10}NR_{11}SO_2R_{12}$, $SO_2NR_{10}NR_{11}R_{12}$, $NR_{10}SO_2NR_{11}NR_{12}R_{13}$ and $NR_{10}SO_2NR_{11}R_{12}$, wherein $R_{10}$, $R_{11}$, $R_{12}$ and $R_{13}$ are independently selected from the group consisting of hydrogen, alkyl and aryl, or a pharmaceutically acceptable salt or prodrug thereof; other than (—)-(11S,2'R)-α-2-piperidinyl-2,8-bis(trifluoromethyl)-4-quinolinemethanol, with the proviso that where $R_1$ and $R_4$ to $R_9$ are hydrogen, $R_2$ or $R_3$ is not 3-methoxy-4-benzyloxyphenyl or 2-dimethylaminoethoxymethyl.

2. A method according to claim 1, wherein $R_1$ is hydrogen or methyl.

3. A method according to claim 1, wherein $R_2$ is hydrogen or methyl.

4. A method according to claim 1, wherein $R_3$ is, selected from the group consisting of methyl, isopropyl, cyclohexyl and benzyl.

5. A method according to claim 1, wherein $R_3$ is a 5 or 6-membered ring.

6. A method according to claim 1, wherein $R_3$ is selected from the group consisting of phenyl, 2-thienyl, 3-thienyl, 2-furyl, 3-furyl and 2-pyridyl.

7. A method according to claim 1, wherein $R_2$ and $R_3$ together form a 5 or 6-membered carbocyclic ring.

8. A method according to claim 1, wherein $R_2$ and $R_3$ together form a 4, 5 or 6-membered saturated or partially unsaturated heterocyclic ring.

9. A method according to claim 1, wherein $R_1$ and $R_2$ or $R_3$ together form a 3, 4, 5, 6, 7 or 8-membered oxygen-containing saturated or partially unsaturated heterocyclic ring.

10. A method according to claim 1, wherein $R_1$ and $R_2$ and $R_3$ together form a 4, 5, 6, 7 or 8 membered oxygen-containing partially unsaturated or aromatic hetexocyclic ring in which $R_2$ and $R_3$ together form a double bond.

11. A method according to claim 7, wherein said carbocyclic or heterocyclic ring when partially unsaturated or aromatic is fused to a phenyl ring.

12. A method according to claim 1, wherein $R_4$, $R_5$, $R_6$, $R_7$, $R_8$ and $R_9$ are independently selected from the group consisting of hydrogen, alkyl, aryl, 4, 5, 6, 7 or 8 membered saturated and heterocyclic rings containing one or more heteroatoms selected from the group consisting of O, S, and N, hydroxy, halogen, nitro, cyano, alkoxy, aryloxy, $COR_{10}$, $OCOR_{10}$, $CO_2R_{10}$, $SR_{10}$, $SR_{10}$, $SOR_{10}$, $SO_2R_{10}$, $SO_2NR_{10}R_{11}$, $CONR_{10}R_{11}$, $CONR_{10}NR_{11}R_{12}$, $OCONR_{10}R_{11}$, $NR_{10}R_{11}$, $NR_{10}COR_{11}$, $NR_{10}CONR_{11}R_{12}$, $NR_{10}CO_2R_{11}$, $NR_{10}SO_2R_{11}$, $CR_{10}NOR_{11}$, $NR_{10}CONR_{11}NR_{12}R_{13}$, $NR_{10}NR_{11}CO_2R_{12}$, $NR_{10}NR_{11}CONR_{12}R_{13}$, $SO_2NR_{10}NR_{11}R_{12}$, $NR_{10}SO_2NR_{11}NR_{12}R_{13}$ and $NR_{10}SO_2NR_{11}R_{12}$, wherein $R_{10}$, $R_{11}$, $R_{12}$ and $R_{13}$ are independently selected from the group consisting of hydrogen, alkyl and aryl.

13. A method according to claim 1, wherein at least one of $R_4$ to $R_9$ is a substituent group other than hydrogen.

14. A method according to claim 1, wherein $R_4$ and/or $R_9$ is a substituent other than trifluoromethyl.

15. A method according to claim 1, wherein $R_5$ is hydrogen or alkyl.

16. A method according to claim 1, wherein $R_5$ is methyl.

17. A method according to claim 1, wherein if any of $R_4$ to $R_9$ are $NR_{10}COR_{11}$ then $R_{10}$ of the $NR_{10}COR_{11}$ group is hydrogen.

18. A method according to claim 1, wherein $R_6$, $R_7$ and/or $R_8$ is hydrogen.

19. A method according to claim 1, wherein the compounds of formula (I) are selected from the group consisting of:
2,8-bis(trifluoromethyl)-α-(3-thienyl)-4-quinolinemethanol;
2,8-bis(trifluoromethyl)-α-cyclohexyl-4-quinolinemethanol;
2,8-bis(trifluoromethyl)-α-(2,6-dichlorophenyl)-4-quinolinemethanol;
2,8-bis(trifluoromethyl)-α-(2-bromophenyl)-4-quinolinemethanol;
2,8-bis(trifluoromethyl)-α-(2-methoxyphenyl)-4-quinolinemethanol;
8-methyl-α-(3-thienyl)-2-trifluoromethyl-4-quinolinemethanol;
α-cyclohexyl-8-methyl-2-trifluoromethyl-4-quinolinemethanol, and
α-cyclohexyl-2-hydroxy-4-quinolinemethanol.

20. A method according to claim 1, wherein the movement disorder is Parkinson's disease.

21. A method according to claim 20 for treatment of drug-induced Parkinsonism, post-encephalitic Parkinsonism, Parkinsonism induced by poisoning or post-traumatic Parkinson's disease.

22. A method according to claim 1, wherein the movement disorder is progressive supernuclear palsy, Huntingtons disease, multiple system atrophy, corticobasal degeneration, Wilsons disease, Hallerrorden-Spatz disease, progressive pallidal atrophy, Dopa-responsive dystonia-Parkinsonism, spasticity or a disorder of the basal ganglia which result is dyskinesias.

23. A method according to claim 1, wherein the compound of formula (I) is in combination with one or more additional drugs useful in the treatment of movement disorders, the components being in the same formulation or in separate formulations for administration simultaneously or sequentially.

24. A method according to claim 23, wherein the one or more additional drugs is L-DOPA.

25. A method according to claim 1, wherein the subject is human.

26. A compound of formula (I):

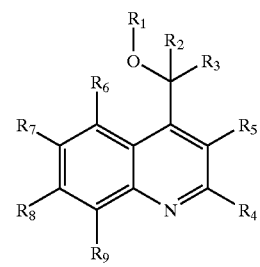

(I)

or a pharmaceutically acceptable salt or prodrug thereof, wherein:

$R_4$, $R_5$, $R_6$, $R_7$, $R_8$ and $R_9$ are independently selected from hydrogen, alkyl, aryl, 4, 5, 6, 7 or 8 membered saturated and partially unsaturated heterocyclic rings containing one or more heteroatoms selected from O, S and N, hydroxy, halogen, nitro, cyano, alkoxy, aryloxy, $COR_{10}$, $OCOR_{10}$, $CO_2R_{10}$, $SR_{10}$, $SOR_{10}$, $SO_2R_{10}$, $SO_2NR_{10}R_{11}$, $CONR_{10}R_{11}$, $CONR_{10}NR_{11}R_{12}$, $OCONR_{10}R_{11}$, $NR_{10}R_{11}$, $NR_{10}COR_{11}$, $NR_{10}CONR_{11}R_{12}$, $NR_{10}CO_2R_{11}$, $NR_{10}SO_2R_{11}$, $CR_{10}NOR_{11}$, $NR_{10}CONR_{11}NR_{12}R_{13}$, $NR_{10}NR_{11}CO_2R_{12}$, $NR_{10}NR_{11}CONR_{12}R_{13}$, $NR_{10}NR_{11}COR_{12}$, $NR_{10}NR_{11}SO_2R_{12}$, $SO_2NR_{10}NR_{11}R_{12}$, $NR_{10}SO_2NR_{11}NR_{12}R_{13}$ and $NR_{10}SO_2NR_{11}R_{12}$ wherein $R_{10}$, $R_{11}$, $R_{12}$ and $R_{13}$ are independently selected from hydrogen, alkyl and aryl, and wherein (i) $R_1$ is hydrogen or alkyl; $R_2$ is selected from hydrogen, alkyl, aryl and 4, 5, 6, 7 or 8 membered unbridged saturated and partially unsaturated heterocyclic rings containing one or more heteroatoms selected from O, S and N; or $R_1$ and $R_2$ together may form a 3, 4, 5, 6, 7 or 8 membered oxygen-containing saturated or partially unsaturated heterocyclic ring optionally containing one or more additional heteroatoms selected from O, S and N; and $R_3$ is a 5 or 6 membered unbridged saturated, partially-unsaturated or aromatic heterocyclic ring containing one or more heteroatoms selected from O and S; and $R_4$ to $R_9$ are as hereinbefore defined; or (ii) $R_1$ is hydrogen or alkyl; $R_2$ is selected from hydrogen, alkyl, aryl and 4, 5, 6, 7 or 8 membered unbridged saturated and partially unsaturated heterocyclic rings containing one or more heteroatoms selected from O, S and N; or $R_1$ and $R_2$ together may form a 3, 4, 5, 6, 7 or 8 membered oxygen-containing saturated or partially unsaturated heterocyclic ring optionally containing one or more additional heteroatoms selected from O, S and N; $R_3$ is a 3, 4, 5, 6 or 7 membered carbocyclic ring; and $R_4$ to $R_9$ are as hereinbefore defined provided that at least one thereof is a substituent group other than hydrogen; or (iii) $R_1$ is hydrogen or alkyl; $R_2$ and $R_3$ together form a 3, 4, 5 or 7 membered saturated or partially-unsatutrated carbocyclic ring, or a 4, 5, 6 or 7 membered saturated or partially-unsatgurated heterocyclic ring in which the one or more heteroatoms are selected only from O and S, or a 4, 5 or 7 membered saturated or partially unsaturated heterocyclic ring containing one or more heteroatoms selected from N; and $R_4$ to $R_9$ are as hereinbefore defined; or (iv) $R_1$ is $C_1$ to $C_4$ acyclic alkyl; $R_2$ is selected from hydrogen, alkyl, aryl and 4, 5, 6, 7 or 8 membered unbridged saturated and partially unsaturated heterocyclic rings containing one or more heteroatoms selected from O, S and N; $R_3$; is aryl or $C_3$ to $C_7$ cycloalky; and $R_4$ to $R_9$ are as hereinbefore defined; or (v) $R_1$ is $C_1$ to $C_4$ acyclic alkyl; $R_2$ and $R_3$ together form a 3, 4, 5, 6 or 7 membered saturated or partially-unsaturated carboyclic ring or a 3,4, 5, 6, 7 or 8 membered saturated or partially unsaturated heterocyclic ring containing one or more heteratoms selected from O, S and N; and $R_4$ to $R_9$ are as hereinbefore defined.

wherein said carbocyclic ring or said heterocyclic ring when partially unsaturated or aromatic is optionally fused to an aryl ring, with the proviso that where $R_1$ and $R_4$ to $R_9$ are hydrogen, $R_2$ or $R_3$ is not 3-methoxy-4-benzyloxyphenyl or 2-dimethylaminoethoxymethyl.

* * * * *